US006534049B2

(12) United States Patent
Laub

(10) Patent No.: US 6,534,049 B2
(45) Date of Patent: *Mar. 18, 2003

(54) SYNTHETIC SOIL-EXTRACT MATERIALS AND MEDICAMENTS FOR HUMAN IMMUNODEFICIENCY VIRUSES BASED THEREON

(75) Inventor: Richard J. Laub, Newport Beach, CA (US)

(73) Assignee: Laub BioChemicals Corp., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/976,557

(22) Filed: Oct. 11, 2001

(65) Prior Publication Data

US 2002/0048561 A1 Apr. 25, 2002

Related U.S. Application Data

(60) Continuation-in-part of application No. 09/345,865, filed on Jul. 1, 1999, which is a division of application No. 08/798,329, filed on Feb. 10, 1997, now Pat. No. 5,945,446.
(60) Provisional application No. 60/254,709, filed on Dec. 11, 2000.

(51) Int. Cl.⁷ .......................... A61K 31/74; A61K 31/35
(52) U.S. Cl. ...................................... 424/78.02; 514/456
(58) Field of Search ........................ 424/78.02; 514/456

(56) References Cited

U.S. PATENT DOCUMENTS

| 4,921,840 A | 5/1990 | Seubert et al. |
| 4,999,202 A | 3/1991 | Cronje et al. |
| 5,284,651 A | 2/1994 | Riede et al. |

FOREIGN PATENT DOCUMENTS

| DE | 3830333 C1 | 3/1990 |
| DE | 0537430 A1 | 4/1993 |
| DE | 41 34 378 A1 | 4/1993 |
| EP | 0119768 A1 | 9/1984 |
| WO | WO 95/08335 | 3/1995 |

OTHER PUBLICATIONS

Derwent Database, Derwent Accession No. 1995–139382, "Treating HIV with humic acid—also stimulates interleukin–2 production and inhibits syncytia formation; humic acid is useful alone or as adjuvant in vaccinations", Mar. 30, 1995 (abstract).*

HealthGate Document—R. Ansorg et al.—Studies on the Antimicrobial Effect of Natural and Synthetic Humic Acids—*Arzeimittelforschung* 1978, 28(12), pp. 2195–2198.

(List continued on next page.)

Primary Examiner—Thurman K. Page
Assistant Examiner—Blessing Fubara
(74) Attorney, Agent, or Firm—Knobbe, Martens, Olson & Bear, LLP

(57) ABSTRACT

Phenolic polymers are prepared by oxidizing and polymerizing starting organic compounds comprising at least one hydroxyl group and at least one carbonyl group or at least two hydroxyl groups on an aromatic structure. One or more inorganic compounds or salts is added and the solution is allowed to stand at about 20° C. to 80° C. for a period of about at least 2 hours. Salt molecules as well as starting compounds and other low molecular-weight materials below about 500 to about 10,000 daltons are removed from the product solution. Purified phenolic polymers are prepared in concentrated aqueous solution or in dried powder form in a final step if necessary. The resultant phenolic polymers exhibit physicochemical properties strongly resembling those of typical commercially-available natural-product soil extracts. The materials are active human immunodeficiency anti-viral agents, and are effective in anti-viral compositions for treating or preventing human immunodeficiency viral diseases.

32 Claims, 4 Drawing Sheets

OTHER PUBLICATIONS

HealthGate Document—K.D. Thiel et al.—Comparison of the in vitro Activities of Ammonium Humate and of Enzymically Oxidized Chlorogenic and Caffeic Acids Against Type 1 and Type 2 Human Herpes Virus—*Pharmazie* 1981, 36(1), pp. 50–53.

HealthGate Document—H. Schultz—Investigations on the Viricidal Effects of Humic Acids in Peat–Mull—*Dtsch Tierarztl Wochenschr* Jul. 1, 1965, 72(13), pp. 294–297.

HealthGate Document—R. Klöcking et al.—Antiviral Properties of Humic Acids—*Experientia* May 15, 1972, 28(5), pp. 607–608 (Article & Abstract).

HealthGate Document—G. Sydow et al.—The Effect of Phenolic Polymers on Retroviruses—*Pharmazie* Dec. 1986, 41(12), pp. 865–868.

HealthGate Document—R. Klöcking et al.—Antiviral Activity of Phenolic Polymers Against Type 1 Herpesvirus Hominis—*Pharmazie* Aug. 1978, 33(8), p. 539.

HealthGate Document—F. Schiller et al.—Results of an Oriented Clinical Trial of Ammonium Humate for the Local Treatment of Herpesvirus Hominus (HVH) Infections—*Dermatol Monatsschr* Jul. 1979, 165(7), pp. 505–509.

HealthGate Document—B. Helbig et al.—Therapeutic Effect of (E)–5–(2–Bromovinyl)–2'–Deoxyuridine, Caffeic Acid Oxidation Product.

And Trisodiumphosphonoformate on Cutaneous Herpes Simplex Virus Type 1 Infection in Guinea Pigs—*J Med Virol* Nov. 1987, 23(3), pp. 303–309.

R. Klöcking—Interaction of Humic Acids and Humic–Acid–Like Polymers with Herpes Simplex Virus Type 1—*Humanic Substances in the Aquatic and Terrestrial Environment*, Berlin 1991, pp. 408–412.

HealthGate Document—in vitro Studies of the Antiviral Activity of Enzymatically Oxidized O–Diphenolic Compounds Against Herpes Simplex Virus Type 1 and 2—*Zentralbl Bakterios (Orig. A)* Mar. 1979, 234(2), pp. 159–169.

HealthGate Document—K.D. Thiel et al.—In vitro Studies of the Antiviral Activity of Ammonium Humate Against Herpes Simplex Virus Type 1 and Type 2—*Zentralbl Bakteriol (Orig. A)* Nov. 1977, 239(3), pp. 304–321.

HealthGate Document—K.D. Thiel et al.—Antiviral Activity of Enzymatically Oxidized Caffeic Acid Against Herpesvirus Hominis Type 1 and Type 2—*Acta Virol* May 1983, 27(3), pp. 200–208.

HealthGate Document—K.D. Thiel et al.—Antiviral Effect of Enzymatically and Nonenzymatically Oxidized Caffeic and Hydrocaffeic Acids Against Herpesvirus Hominis Type 1 and Type 2 in vitro—*Pharmazie* Nov. 1984, 39(11), pp. 781–782.

M. Cushman et al.—Preparation and Anti–HIV Activities of Aurintricarboxylic Acid Fractions and Analogues: Direct Correlation of Antiviral Potency with Molecular Weight—*Journal of Medicinal Chemistry* 1991, 34(1), pp. 329–337.

M. Cushman et al.—Synthesis and Anti–HIV Activities of Low Molecular Weight Aurintricarboxylic Acid Fragments and Related Compounds—*Journal of Medicinal Chemistry* 1991, vol. 34, pp. 337–342.

HealthGate Document—D. Schols et al.—(Abstract & article) Selective Inhibitory Activity of Polyhydroxcarboxylates Derived From Phenolic Compounds Against Human Immunodeficiency Virus Replication—*J Acquir Immune Defic Syndr* 1991, 4(7), pp. 677–685.

S. Loya et al.—Hexaprenoid Hydroquinones, Novel Inhibitors of the Reverse Transcriptase of Human Immunodeficiency Virus Type 1—*Journal of Natural Products*Dec. 1993, 56(12), pp. 2120–2125.

J. Schneider et al.—Inhibition of HIV–1 in Cell Culture by Synthetic Humate Analogues Derived From Hydroquinone: Mechanism of Inhibition—*Virology* 1996, 218(2), pp. 389–395.

HealthGate Document—J. Hills et al.—Inhibition of Several Strains of Influenza Virus Type A and B by Phenolic Polymers—*Biomed Biochim Acta* 1986, 45(9), pp. 1173–1179 (including German article).

A. Jankowski et al.—A Randomized, Double–Blind Study on the Efficacy of Tolpa Torf Preparation (TTP) in the Treatment of Recurrent Respiratory Tract Infections—*Arch Immunol Ther Exp (Warsz)* 1993, 41(1), pp. 95–97.

R. Klöcking et al.—Title?—*Pharmazie* 1977, 32, p. 297.

HealthGate Document—R. Mentel, et al. "Effectiveness of Phenol Body Polymers Against Influenza Virus A/Krasnodar/101/59H2N2" *Biomed Biochem Acta* 1983 42 (10). pp. 1353–1356.

HealthGate Document—R. Klöcking et al.—Preparation, Characterization and Antiviral Activity of Phenolic Polymers. 2. Antiviral Activity of Phenolic Polymers (Proceedings)—*Pharmazie* May 1979, 34(5–6), pp. 293–294.

HealthGate Document—H.P. Klöcking et al.—Effect of Phenol Ring Polymers on the Release of Plasminogen Activators—*Farmakol Toksikol* Jan.–Feb. 1984, 47(1), pp. 93–95.

K.I. Hanninen et al.—Synthesis and Characterization of Humic Acid–Like Polymers—*The Science of the Total Environment* 1987, 62, pp. 201–210.

HealthGate Document—M. Robert–Gero et al.—Biochemical Study of Humus Action of a Proteolytic Enzyme on Natural and Synthetic Humic Polymers and Those of Microbial Origin—*Ann Inst Pasteur (Paris)* Dec. 1967, 113(6), pp. 903–909.

HealthGate Document—M. Jakubiec et al.—Comparison of the Effect of Natural and Synthetic Humates and EDTA on the Growth of *Escherichia coli*—**Abstract not available.

HealthGate Document—J. Pommery et al.—SOS Chromotest Study Concerning Some Appreciation Criteria of Humic Substances' Genotoxic Potency—*Mutat Res* Jun. 1989, 223(2), pp. 183–189.

HealthGate Document –F.J. Lu, et al., Department of Biochemistry et al.—Humic Acid: Inhibitor of Plasmin—*Sci Total Environ* Apr. 1992, 114, pp. 135–139.

HealthGate Document—K. Wiegleb et al.—The Use of the HET–Cam Test for the Determination of the Irritating Effects of Humic Acids—*DTW Dtsch Tierarztl Wochenschr* Oct. 1993, 100(10), pp. 412–416.

HealthGate Document—W. Seffner—Subchronic Application of Humic Acids and Associated Compounds Provokes Histological Changes of Goitre in the Rat—*Exp Toxicol Pathol* Jan. 1995, 47(1), pp. 63–70.

HealthGate Document—J. Schneider—Inhibition of HIV–1–Cell Culture by Synthetic Humate Analogues Derived From Hydroquinone Mechanism of Inhibition—*Virology* Apr. 15, 1996, 218(2), pp. 389–395.

Hassett et al., "Humic Acids: Synthesis, Properties and Assimilation of Yeast Biomass" *Soil Biol. Biochem*, vol. 20, No. 2 pp. 227–231, 1988.

Shindo, "Catalytic Effect of Volcanic Ash on the Formation of Humic Polymers in Ando Soils" *The Science of the Total Environment*, 117/118 (1992) 63–101.

"Sulfated Polysaccharides Are Potent and Selective Inhibitors of Various Enveloped Viruses, Including Herpes Simplex Virus, Cytomegalovirus, Vesicular Stomatitis Virus, and Human Immunodeficiency Virus"—Masanori Baba, Robert Snoeck, Rudi Pauwels, and Erik De Clercq. Antimicrobial Agents and Chemotherapy, Nov. 1988, p. 1742–1745, vol. 32, No. 11.

Comparison of Core Antigen (p24) Assay and Reverse Transcriptase Activity for Detection of Human Immunodeficiency Virus Type 1 Replication—Sally Land, Fiona Beaton, Dale A. McPhee and Ian D. Gust, *Journal of Clinical Microbiology*, Mar. 1989, p. 486–489, vol. 27, No. 3.

D. Schewe et al. "Lipoxygenase–Inhibitory Action of Antiviral Polymeric Oxidation Porducts of Polyphenols" *Biomed Biochem Acta* 50 (1991) 3, 299–305.

H.L. Yang, et al., "Humic Acid Induces Expression of Tissue Factor by Cultured Endothelial Cells: Regulation by Cytosolic Calcium and Protein Kinase C," *Thromb Haemost* Mar. 1994, 71 (3). pp. 325–330.

* cited by examiner

SYNTHETIC SOIL-EXTRACT MATERIALS AND MEDICAMENTS FOR HUMAN IMMUNODEFICIENCY VIRUSES BASED THEREON

CROSS REFERENCE TO RELATED APPLICATION

This application claims benefit under 35 U.S.C. § 119(e) of U.S. Provisional Application Serial No. 60/254,709, filed Dec. 11, 2000 and is a continuation-in-part of application Ser. No. 09/345,865, filed Jul. 1, 1999, which is a divisional of application Ser. No. 08/798,329, filed Feb. 10, 1997, now U.S. Pat. No. 5,945,446, issued Aug. 31, 1999.

BACKGROUND OF THE INVENTION

1. Field of the Invention

This invention relates to synthetic soil extract substances comprising phenolic polymers, and to compositions and methods for employing the synthetic phenolic polymers for preventing, reducing, treating, or eliminating human immunodeficiency viral diseases.

2. Description of the Related Art

Soil extract materials, particularly the classes of substances known collectively as "humus," "humics," "humic acid(s)," or "humates," have been widely used in a number of applications for many years, as reviewed by F. J. Stevenson, *Humus Chemistry. Genesis Composition Reactions;* New York: Wiley, 1964; and, more recently, by A. Piccolo, *Humic Substances in Terrestrial Ecosystems;* New York: Elsevier, 1996.

Humic substances have long been known to exhibit antiviral properties (H. Schultz, *Dtsch. Tierarztl. Wochenschr.* 1962, 69, 613; 1965, 72(13), 294–297; R. Klocking and M. Sprossig, *Experientia* 1972, 28(5), 607–608), particularly retroviruses (G. Sydow, V. Wunderlich, R. Klocking, and B. Helbig, *Pharmazie* 1986, 41(12), 865–868). Viral pathogens for which soil-extract materials have been shown to be effective include in particular Coxsackie virus A9 (Griggs-Baylor) (R. Klocking and M. Sprossig, *Experientia* 1972, 28(5), 607–608), herpes simplex virus type 1 (B. T. Rouse (Ed.), *Herpes Simplex Virus;* Berlin: Springer-Verlag, 1992; R. Klocking, K. D. Thiel, P. Wutzler, B. Helbig, and P. Drabke, *Pharmazie* 1978, 33(8), 539; F. Schiller, R. Klocking, P. Wutzler, and I. Farber, *Dermatol. Monatsschr.* 1979, 165(7), 505–509; B. Helbig, A. Sauerbrei, R. Klocking, P. Wutzler, N. Wicht, U. Wiedemann, and G. Herrmann, *J. Med. Virol.* 1987, 23(3), 303–309; R. Klocking and B. Helbig, in *Humic Substances in the Aquatic and Terrestrial Environment;* Berlin: Springer-Verlag, 1991; 407–412;) and type 2 (anon. *ZentralbL. Bakteriol* [*Orig. A*] 1976, 234(2), 159–169; K. D. Thiel, R. Klocking, H. Schweizer, and M. Sprossig, *Zentralbl. Bakteriol* [*Orig. A*] 1977, 239(3), 304–321; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782); human immunodeficiency virus (HIV) (M. Cushman, P. Wang, S. H. Chang, C. Wild, E. De Clercq, D. Schols, M. E. Goldman, and J. A. Bowen, *J. Med. Chem.* 1991, 34(1), 329–337; M. Cushman, S. Kanamathareddy, E. De Clercq, D. Schols, M. E. Goldman, and J. A. Bowen, *J. Med. Chem.* 1991, 34(1), 337–342; D. Schols, P. Wutzler, R. Klocking, B. Helbig, and E. De Clercq, *J. Acquir. Immune Defic. Syndr.* 1991, 4(7), 677–685; S. Loya, R. Tal, A. Hizi, S. Issacs, Y. Kashman, and Y. Loya, *J. Nat. Prod.* 1993, 56(12), 2120–2125; J. Schneider, R. Weis, C. Manner, B, Kary, A. Werner, B. J. Seubert, and U. N. Riede, *Virology* 1996, 218(2), 389–395; influenza virus type A (Krasnodar/101/59/H2N2) (R. Mentel, B. Helbig, R. Klocking, L. Dohner, and M. Sprossig, *Biomed. Biochim. Acta* 1983, 42(10), 1353–1356); and type B (J. Hils, A. May, M. Sperber, R. Klocking, B. Helbig, and M. Sprossig, *Biomed. Biochim. Acta* 1986, 45(9), 1173–1179); as well as other respiratory tract infectious agents (A. Jankowski, B. Nienartowicz, B. Polanska, and A. Lewandowicz-Uszyuska, *Arch. Immunol. Ther. Exp.* (*Warsz*) 1993, 41(1), 95–97).

The mechanisms whereby humic substances inhibit the cytopathicity of a number of viruses have been studied in some detail. It is thought that the materials prevent viral replication in part by sorbing onto the viral envelope protein (gp120 in the case of HIV), and thereby block the sorption of viral particles to cell surfaces: K. D. Thiel, R. Klocking, H. Schweizer, and M. Sprossig, *ZentralbL. Bakteriol.* [*Orig. A*] 1977, 239(3), 304–321; D. Schols, P. Wutzler, R. Klocking, B. Helbig, and E. De Clercq, *J. Acquir. Immune Defic. Syndr.* 1991, 4(7), 677–685; anon., *Fortschr. Med.* 1995, 113(7), 10; J. Schneider, R. Weis, C. Manner, B. Kary, A. Werner, B. J. Seubert, and U. N. Riede, *Virology* 1996, 218(2), 389–395. [Extracellular interception of pathogens by chemical agents that bind to them is a well-known means of immunological defense (D. M. Shankel, S. Kuo, C. Haines, and L. A. Mitscher, in *Antimutagenesis and Anticarcinogenesis Mechanisms III;* G. Bronzetti, H. Hayatsu, S. De Flora, M. D. Waters, and D. M. Shankel (Eds.); New York: Plenum, 1993; 65–74). Such materials might well be termed "despathogens", following the terminology proposed by T. Kada and K. Shimoi, *Bioessays* 1987, 7, 113–116, regarding "desmutagens".] It has also been found that naturally-occurring humic acid preparations can stimulate the production of cytokines, including interferon-gamma, interferon-alpha, and tumor necrosis factor-alpha (A. D. Inglot, J. Zielinksa-Jenczylik, and E. Piasecki, *Arch. Immunol. Ther. Exp.* (Warsz) 1993, 41(1), 73–80); as well as interferon-beta (Z. Blach-Olszewska, E. Zaczynksa, E. Broniarek, and A. D. Inglot, *Arch. Immunol. Ther. Exp.* (Warsz), 1993, 41(1), 81–85).

The toxicity of naturally-occurring humic acids is remarkably low (K. D. Thiel, B. Helbig, R. Klocking, P. Wutzler, M. Sprossig, and H. Schweizer, *Pharmazie* 1981, 36(1), 50–53; U. N. Riede, I. Jonas, B. Kim, U. H. Usener, W. Kreutz, and W. Schlickewey, *Arch. Orthop. Trauma Surg.* 1992, 111(5), 259–264; H. Czyzewska-Szafran, Z. Jastrzebski, D. Soltysiak-Pawluczak, M. Wutkiewicz, A. Jedrych, and M. Remiszewska, *Acta Pol. Pharm.* 1993, 50(4–5), 373–377; H. L. Yang, F. J. Lu, S. L. Wung, and H. C. Chiu, *Thromb. Haemost.* 1994, 71(3), 325–330). [Cytotoxic effects of anti-viral substances, including humic acids, are usually evaluated via biological (viability and alterations of cell morphology) and biochemical testing methods ($^{51}Cr$ release), as described by K. D. Thiel, U. Eichhorn, H. Schweizer, and R. Klocking, *Arch. Toxicol. Suppl.* 1980, 4, 428–430.] The cytotoxicity ($CD_{50}$) of a naturally-occurring humic acid for human peripheral blood leukocytes (PBL) was found to be 1–9 milligrams per milliliter. In addition, J. Schneider, R. Weis, C. Manner, B. Kary, A. Werner, B. J. Seubert, and U. N. Riede, *Virology* 1996, 218(2), 389–395, reported that the cytotoxicity of a synthetic humic acid prepared from hydroquinone for MT-2 cells was approximately 600 micrograms per milliliter. It has also been found that medicaments prepared from humic acids isolated from naturally-occurring soil materials are neither carcinogenic (Syrian hamster embryo cell transformation test: J. Koziorowska and E. Anuiszewska, *Acta Pol. Pharm.* 1994, 51(1), 101–102) nor mutagenic (T. Sato, Y. Ose, and H. Hagase, *Mutat. Res.* 1986, 162(2), 173–178; V. M. Sui, A. I. Kiung, and T. I. Veidebaum, *Vopr. Kurortol. Fiozioter. Lech. Fiz. Kult.* 1986, 2(3–4), 34–37; J. Koziorowska, B. Chlopkiewicz, and E. Anuszewska, *Acta Pol. Pharm.* 1993, 50(4–5), 379–382). Prenatal (S. Golbs, V. Fuchs, M. Kuhnert, and C. Polo, *Arch. Exp. Veterinarmed.* 1982, 36(2), 179–185) and embryotoxic and teratogenic effects (T. Juszkiewicz, M. Minta, B. Wlodarczyk, B. Biernacki, and J. Zmudzki, *Acta Pol. Pharm.* 1993, 50(4–5), 383–388) are also not observed with humic preparations at daily dose levels from 5–50 milligrams per kilogram body weight. Topical preparations are tolerated even better (V. V. Soldatov and M. N. Cherepanova, *Vopr. Kurortol. Fizioter. Lech. Fiz. Kult.* 1970, 35(3), 256–259; H. Czyzewska-Szafran, Z. Jastrzebski, D. Soltysiak-Pawluczuk, M. Wutkiewicz, A. Jedrych, and M. Remiszewska, *Acta Pol. Pharm.* 1993, 50(4–5), 373–377) when applied dernally in aqueous solution in amounts as high as 10 percent weight-by-volume (K. Wiegleb, N. Lange, and M. Kuhnert, *Dtsch. Tierarztl. Wochenschr.* 1993, 100(10), 412–416).

Because humic substances are not chemically well-defined, the preparation of synthetic humic acids whose physicochemical properties mimic naturally-occurring materials is quite difficult, as pointed out by K. Murray and P. W. Linder, *J. Soil Sci.* 1983, 34, 511–523. Nevertheless, there have been several notable advances in this area. Broadly speaking, three general strategies have evolved. All depend upon starting with well-defined molecules of molecular weight on the order of hydroxybenzoic acid, and then causing the molecules to polymerize upon themselves to form larger molecules. The methods differ in the causation factor, which can be microbial, chemical, or enzymatic.

Humic acids of microbial origin have been described and discussed by M. Robert-Gero, C. Hardisson, L. Le Borgne, and G. Pignaud, *Ann. Inst. Pasteur* (Paris) 1966, 111(6), 750–767; and by M. Robert-Gero, C. Hardisson, L. Le Borgne, and G. Vidal, *Ann. Inst. Pasteur* (Paris) 1967, 113(6), 903–909.

The chemical synthesis of humic acids has been pioneered by R. Klocking, B. Helbig, and associates: R. Klocking, B. Helbig, and P. Drabke, *Pharmazie* 1977, 32, 297; R. Klocking, B. Helbig, K. D. Thiel, T. Blumohr, P. Wutzler, M. Sprossig, and F. Schiller, *Pharmazie* 1979, 34(5–6), 293–294; R. Mentel, B. Helbig, R. Klocking, L. Dolner and M. Sprossig, *Biomed. Biochim. Acta* 1983, 42(10), 1353–1356; H. P. Klocking, R. Klocking, and B. Helbig, *Farmakol Toksikol.* 1984, 47(1), 93–95; K. D. Thiel, P. Wutzler, B. Helbig, R. Klocking, M. Sprossig, and H. Schweizer, *Pharmazie* 1984, 39(11), 781–782; J. Hils, A. May, M. Sperber, R. Klocking, B. Helbig, and M. Sprossig, *Biomed. Biochim. Acta* 1986, 45(9), 1173–1179; B. Helbig, A. Sauerbrei, R. Klocking, P. Wutzler, N. Wicht, U. Wiedemann, and G. Herrmann, *J. Med. Virol.* 1987, 23(3), 303–309; K. I. Hanninen, R. Klocking, and B. Helbig, *Sci. Total Environ.* 1987, 62, 201–210; R. Klocking and B. Helbig, in *Humic Substances in the Aquatic and Terrestrial Environment*; New York: Springer-Verlag, 1989; 407–412; C. Schewe, R. Klocking, B. Helbig, and T. Schewe, *Biomed. Biochim. Acta* 1991, 50(3), 299–305; D. Schols, P. Wutzler, R. Klocking, B. Helbig, and E. De Clercq, *J. Acquir. Immune Defic. Syndr.* 1991, 4(7), 677–685. Typically, 10 millimoles of the starting small-molecule phenolic compound is dissolved in distilled water, the pH is adjusted to 8.5 with aqueous sodium hydroxide (NaOH), and then 2–5 millimoles of sodium periodate ($NaIO_4$) is added. The solution is warmed at 50° C. for 30 minutes, and is then allowed to stand overnight. The resultant humic acid-like polymeric products are isolated by precipitation with lead(II) nitrate [$Pb(NO_3)_2$]. The precipitated polymers are redissolved in aqueous sodium hydroxide (pH 8.5) and heated with 8-hydroxyquinoline for 30 minutes at 100° C. The precipitate formed is lead(II) chelate, which is removed by filtration. Residual 8-hydroxyquinoline is extracted with chloroform, and the desired polymeric material is then precipitated from the aqueous solution by the addition of various combinations of acetic acid, ethyl acetate, and ethanol. Starting compounds that have been used for the synthesis of humic-like materials include 4-[bistp-hydroxyphenyl)methylene]-2,5-cyclohexadien-1-one (aurin), 4-[bis(3-carboxy-4-hydroxyphenyl)methylene]-2-carboxy-2,5-cyclohexadien-1-one (aurintricarboxylic acid), 3-(3,4-dihydroxyphenyl)propenoic acid (caffeic acid), 1,2-dihydroxybenzene (catechol), 1,3,4,5-tetrahydroxycyclohexanecarboxylic acid 3-(3,4-dihydroxyphenyl)propenoate (chlorogenic acid), 3,4-dihydroxyphenylacetic acid (homoprotocatechuic acid), 1-(3,4-dihydroxyphenyl)-2-(N-methylamino)ethanol (epinephrine), 3-(4-hydroxy-3-methoxyphenyl)-2-propenoic acid (ferulic acid), 3,4-5-trihydroxybenzoic acid (gallic acid), 2,5-dihydroxybenzoic acid (gentisic acid), 2,5-dihydroxyphenylacetic acid (homogentisic acid), 3-(3,4-dihydroxyphenyl)propionic acid (hydrocaffeic acid), 1,4-dihydroxybenzene (hydroquinone), 2,3-dihydroxytoluene (3-methylcatechol), 3,4-dihydroxytoluene (4-methylcatechol), 2,5-dihydroxytoluene (2-methylhydroquinone), 4,4'-(2,3-dimethyltetramethylene)-di-(1,2-dihydroxybenzene) (nordihydroguaiaretic acid), 1-(3,4-dihydroxyphenyl)-2-aminoethanol (norepinephrine), 3,4-dihydroxybenzoic acid (protocatechuic acid), 1,2,3-trihydroxybenzene (pyrogallol), 1,3-dihydroxybenzene (resorcinol), and 4-hydroxy-3-methoxybenzoic acid (vanillic acid). Other notable efforts on the chemical synthesis of humic-like substances include the studies by De Clercq and colleagues on aurintricarboxylic acid, its derivatives, and related compounds: M. Cushman, P. Wang, S. H. Chang, C. Wild, E. De Clercq, D. Schols, M. E. Goldman, and J. A. Bowen, *J. Med. Chem.* 1991, 34(1), 329–337; M. Cushman, S. Kanamnathareddy, E. De Clercq, D. Schols, M. E. Goldman, and J. A. Bowen, *J. Med. Chem.* 1991, 34(1), 337–342. Related efforts have also been reported by M. Robert-Gero, C. Hardisson, L. Le Borgne, and G. Vidal, *Ann. Inst. Pasteur* (Paris) 1967, 113(6), 903–909; M. Jakubiec, E. Miszczak, and J. Szczerkowska, *Acta Microbiol. Pol.* [B] 1971, 3(1), 63–66; R. Ansorg and W. Rochus, *Arzneimitteiforschung* 1978, 28(12), 2195–2198; J. Pommery, M. Imbenotte, A. F. Urien, D. Marzin, and F. Erb, *Mutat. Res.* 1989, 223(2), 183–189; F. J. Lu and Y. S. Lee, *Sci. Total Environ.* 1992, 114, 135–139; K. Wiegleb, N. Lange, and M. Kuhnert, *DTW Dtsch. Tierarztl. Wochenschr.* 1993, 100(10), 412–416; H. L. Yang, F. J. Lu, S. L. Wung, and H. C. Chiu, *Thromb. Haemost.* 1994, 71(3), 325–330; W. Seffner, F. Schiller, R. Heinze, and R. Breng, *Exp. Toxicol. Pathol.* 1995, 47(1), 63–70; and J. Schneider, R. Weis, C. Manner, B. Kary, A. Werner, B. J. Seubert, and U. N. Riede, *Virology* 1996, 218(2), 389–395.

The enzymatic catalytic synthesis of humic acids dates to about 1961 with the work by R. E. Hampton and R. W. Fulton, *Virology* 1961, 13, 44–52 (see also R. E. Hampton, *Phytophathology* 1970, 60, 1677–1681), who found that enzymatically oxidized phenols inactivate phytopathogenic (i.e., plant-related) viruses. Typically o-diphenol oxidase has been employed for the enzymatic synthesis of humic-like materials: anon. *Zentralbl. Bakteriol.* [*Orig A*] 1976, 234(2), 159–169; R. Klocking, B. Helbig, and P. Drabke, *Pharmazie* 1977, 32(5), 297; K. D. Thiel, B. Helbig, R. Klocking, P. Wutzler, M. Sprossig, and H. Schweizer, *Pharmazie* 1981, 36(1), 50–53; K. D. Thiel, B. Helbig, M. Sprossig, R. Klocking, and P. Wutzler, *Acta Virol.* 1983, 27(3), 200–208; K. D. Thiel, P. Wutzler, B. Helbig, R. Klocking, M. Sprossig, and H. Schweizer, *Pharmazie* 1984, 39(11), 781–782; and G. Sydow, V. Wunderlich, R. Klocking, and B. Helbig, *Pharmazie* 1986, 41(12), 865–868.

A direct comparison of humic acids synthesized enzymatically and nonenzymatically from caffeic and hydrocaffeic acids has shown that the two synthetic routes produce materials that differ somewhat in their efficacy for the suppression of herpes (hominis) types 1 and 2 viruses: K. D. Thiel, P. Wutzler, B. Helbig, R. Klocking, M. Sprossig, and H. Schweizer, *Pharmazie* 1984, 39(11), 781–782.

PCT application WO 00/16785 (Mar. 30, 2000) from Dekker and Medlen discloses the use of humic acid or its salts, esters, or derivatives thereof, all prepared as described in U.S. Pat. Nos. 4,912,256 and 5,004,831 from coal extracts, in stimulating lymphocytes in a human, animal, or bird. This allows for the treatment of viral and bacterial infections, and more particularly HIV infections, cancer, and opportunistic diseases. Oxihumic acids, salts, esters, or derivatives thereof are preferred. Administration is preferably oral. Some example pharmacological data presented include the antiviral activity of oxihumates against HIV-1 in vitro and clinical trials of oral oxihumate in HIV-infected patients.

PCT application WO 00/16786 (Mar. 30, 2000) from Dekker and Medlen discloses the use of pharmaceutical compositions comprising an oxihumic acid or its salts, esters, or derivatives thereof, all prepared as described in U.S. Pat. Nos. 4,912,256 and 5,004,831 from coal extracts, as active ingredients. Compositions are preferably administered orally for stimulating lymphocytes in a human, animal, or bird. They may be used in treating viral and bacterial infections, HIV infections, opportunistic diseases, inflammation, pain and fever, cancer growth, and diseases associated with viral infection and a depressed immune system. A number of pharmacological examples are given, including interleukin 10 production by oxihumate-treated lymphocytes, increased antibody production against Newcastle disease in chickens treated with oxihumate, TNF production by oxihumate-treated lymphocytes, and antiviral activity of oxihumate against HSV-1 and coxsackie virus type 1 in vitro.

The diversity of physicochemical characteristics as well as wide variation in the biological activity and toxicity of humics extracted or otherwise derived from natural soils has been well documented. This diversity and variation is due to variations in factors such as the source of the soil, the method(s) of extraction and/or isolation, and the technique(s) employed to treat the extract once it has been separated and isolated from crude soil. The consequence of irreproducibility of the properties of substances extracted from natural soil is that the commercial value of such materials is minimized. In addition, they are rendered unsuitable as medicaments. Also, while a number of laboratory-scale processes have already been described that address various aspects of the isolation, synthesis, and/or preparation of humic substances or similar materials, there are no reports of preparing and isolating such purely synthetic humic acids or similar materials by methods that are suitable for scaleup directly to industrial levels, that provide economically acceptable yields, and that optimize the preparation procedures from the standpoint of medicament safety and efficacy. Also, all of the known synthetic methods utilize potentially toxic precipitation methods, such as lead(II) nitrate precipitation; followed by complex isolation procedures, such as potentially mutagenic compound-producing hydrochloric acid precipitation; or lengthy synthetic steps as long as 10 days.

SUMMARY OF THE INVENTION

There is a need to devise simple synthetic procedures that yield inexpensive, safe materials whose physicochemical attributes are reproducible, and that at least simulate those of typical commercially-available soil extracts. There is a need for a safe, efficacious and simple method for treating blood products, especially human blood products, to reduce or eliminate lipid enveloped and non-enveloped virus activity without loss of blood product or blood product activity.

One embodiment is a method for preventing and/or treating human immunodeficiency virus infection in a mammal which comprises administering an effective amount of a synthetic phenolic polymeric material which is prepared by:
A) Dissolving the starting organic compound or mixture of organic compounds in an aqueous solution;
B) Oxidizing and polymerizing the organic compound or mixture of organic compounds;
C) Adding one or more compounds or salts selected from the group consisting of boric acid, borate salts, alkaline earth salts, transition metal salts, alkaline sulfides, alkaline earth sulfides or transition metal sulfides to the aqueous solution resulting from step B);
D) Allowing the aqueous solution resulting from step C) to stand with or without stirring at between about 20° C. and 100° C. for a period of at least about 2 hours; and
E) Removing molecules from the solution resulting from step F) below about 500 daltons to 10,000 daltons.

In another aspect, the step of oxidizing and polymerizing the starting organic compound can be achieved by adjusting the pH of the aqueous solution to between about 8 and 11, adding an alkaline periodate or alkaline-earth periodate salt to the aqueous solution, and maintaining the temperature of the solution between about 20° C. and 1 00° C. for a period of at least about 30 minutes.

In another aspect, the method of preparation of the synthetic phenolic polymeric material further comprises a step, following the step of removing molecules from the solution below about 500 daltons to 10,000 daltons, of concentrating the solution.

In another aspect, the method of preparation of the synthetic phenolic polymeric material further comprises a step, following the step of removing molecules from the solution below about 500 dalton to 10,000 daltons, of removing water from the solution.

In another aspect, the human immunodeficiency virus infection is effected by a virus, preferably HIV-1 or HIV-2.

In another aspect, the administering of a synthetic phenolic polymeric material is along with an effective amount of an antiviral composition.

In another aspect, the administering of a synthetic phenolic polymeric material can be achieved systemically or topically.

One embodiment is a method for inhibiting human immunodeficiency viral attachment to host cells in a mammal which comprises administering an effective amount of a synthetic phenolic polymeric material which is prepared by:
A) Dissolving the starting organic compound or mixture of organic compounds in an aqueous solution;

B) Oxidizing and polymerizing the organic compound or mixture of organic compounds;

C) Adding one or more compounds or salts selected from the group consisting of boric acid, borate salts, alkaline earth salts, transition metal salts, alkaline sulfides, alkaline earth sulfides or transition metal sulfides to the aqueous solution resulting from step B);

D) Allowing the aqueous solution resulting from step C) to stand with or without stirring at between about 20° C. and 1 00° C. for a period of at least about 2 hours; and E) Removing molecules from the solution resulting from step F) below about 500 daltons to 10,000 daltons.

In another aspect, the step of oxidizing and polymerizing the starting organic compound can be achieved by adjusting the pH of the aqueous solution to between about 8 and 11, adding an alkaline periodate or alkaline-earth periodate salt to the aqueous solution, and maintaining the temperature of the solution between about 20° C. and 1 00° C. for a period of at least about 30 minutes.

In another aspect, the method of preparation of the synthetic phenolic polymeric material further comprises a step, following the step of removing molecules from the solution below about 500 daltons to 10,000 daltons, of concentrating the solution.

In another aspect, the method of preparation of the synthetic phenolic polymeric material further comprises a step, following the step of removing molecules from the solution below about 500 dalton to 10,000 daltons, of removing water from the solution.

DETAILED DESCRIPTION OF THE PREFERRED EMBODIMENT

Figure 1:
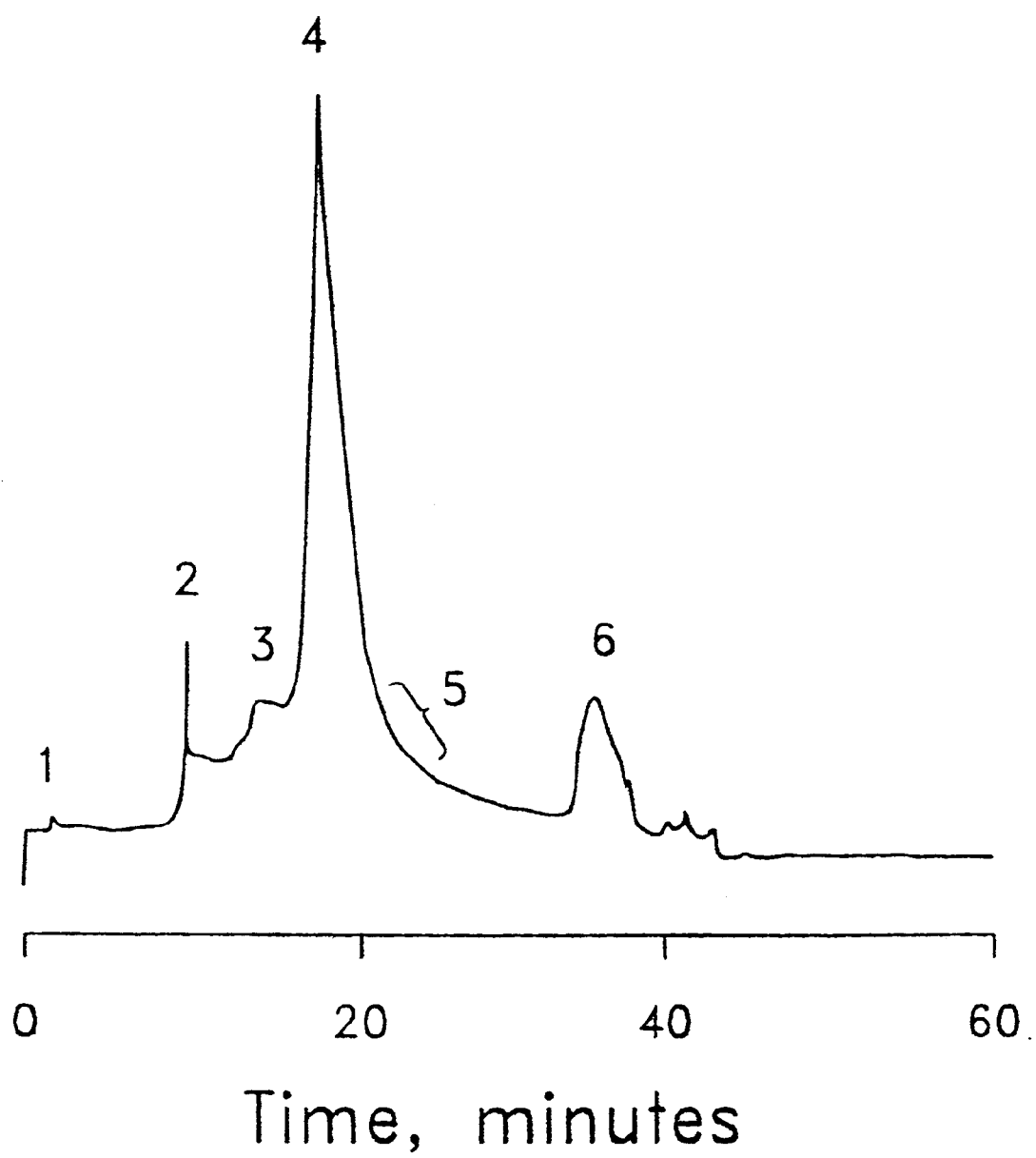
FIG. 1 shows a high-performance liquid chromatography (HPLC) trace for the synthetic humic acid product obtained from 2,5-dihydroxyphenylacetic acid (homogentisic acid), as described in Examples 10, 11, and 12.

U.S. Pat. No. 5,945,446, issued Aug. 31, 1999, discloses the process for preparing synthetic soil-extract materials and medicaments based thereon. U.S. Pat. No. 5,945,446 and the references therein are incorporated herein by reference in their entirety.

The inventor has developed combinations of chemical processes for the preparation of synthetic phenolic polymeric materials, also known as synthetic humic acids, whose physicochemical properties and attributes are reproducible, and which simulate those of typical commercially-available natural humic acids and other soil extracts, which contain little or no ionic salts or other compounds of molecular weight less than 500 daltons, which have a minimum molecular weight of 500 daltons, and which processes shall be suitable for scaleup directly to industrial levels that provide economically acceptable yields.

The inventor has also developed compositions and methods for treating or preventing human immunodeficiency viral diseases by using an effective amount for anti-viral activity of a synthetic humic acid prepared according to the above processes.

The starting compounds used in the chemical processes employed for production of synthetic humic acids according to particularly preferred embodiments are known materials that are readily available commercially.

A preferred embodiment of the chemical processes for the preparation of synthetic humic acids includes the following steps:

A) Dissolving the starting organic compound or mixture of organic compounds in an aqueous solution;

B) Adjusting the pH of the aqueous solution resulting from step A) to between about 8 and 11 if necessary;

C) Adding an alkaline periodate salt or alkaline-earth periodate salt, to the aqueous solution resulting from step B);

D) Maintaining the temperature of the solution resulting from step C) between about 20° C. and 100° C. for a period of at least about 30 minutes;

E) Adding one or more compounds or salts selected from the group consisting of boric acid, borate salts, alkaline earth salts, transition metal salts, alkaline sulfides, alkaline earth sulfides or transition metal sulfides to the aqueous solution resulting from step D);

F) Allowing the aqueous solution resulting from step E) to stand with or without stirring at a temperature between about 20° C. and 100° C. for a period of at least about 2 hours;

G) Removing molecules from the solution resulting from step F) below about 500 daltons to 10,000 daltons;

H) Concentrating the solution resulting from step G); and

I) Removing the water from the solution resulting from step H), if necessary.

The starting organic compound in step A) above can be one, or more than one in combination, of different organic compounds comprising at least one hydroxyl group and at least one carbonyl group or at least two hydroxyl groups on an aromatic structure. The Examples herein include both types of starting organic compounds. Examples of compounds comprising at one hydroxyl group and at least one carbonyl group include aurintricarboxylic acid and tetrahydroxybenzoquinone. Examples of starting organic compounds comprising at least two hydroxyl groups on an aromatic structure include hydroquinone and norepinephrine.

Particularly preferred starting organic compounds are illustrated in Tables 1 and 2. Starting organic compounds illustrated in Table 1 are comprised of a single benzene ring with six substituents $R_1$–$R_6$, wherein $R_1$–R6 can be any one of the indicated atom or functional groups, as long as at least one of $R_1$–R6 is a hydroxy (—OH) functional group. Preferably, at least one of $R_1$–$R_6$ is a hydroxy (—OH) functional group and at least one of the remaining substituents $R_1$–$R_6$ contains a carboxylic acid functional group. More preferably, two of $R_1$–$R_6$ are hydroxy (—OH) functional groups and one of the remaining substituents $R_1$–$R_6$ contains a carboxylic acid functional group. Homogentisic acid, which is 2,5-dihydroxyphenylacetic acid, is a particularly preferred starting organic compound. Caffeic acid, which is 3,4-dihydroxycinnamic acid, is another particularly preferred starting organic compound. Chlorogenic acid, which is 1,3,4,5-tetrahydroxycyclohexanecarboxylic acid 3-(3,4-dihydroxycinnamate) is yet another particularly preferred starting organic compound.

TABLE 1

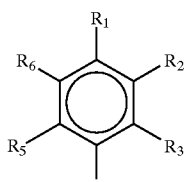

$R_1, R_2, R_3, R_4, R_5, R_6 =$

—H
—$CH_3$
—$CH_2CH_3$
—$(CH_2)_2CH_3$
—$CH(CH_3)_2$
—OH
—$OCH_3$
—CHO
—$CO_2H$
—$CO_2CH_3$
—$CH_2OH$
—$CH_2OCH_3$
—$CH_2CHO$
—$CH_2CO_2H$
—$CH_2CO_2CH_3$
—$(CH_2)_2OH$
—$(CH_2)_2OCH_3$
—$(CH_2)_2CHO$
—$(CH_2)_2CO_2H$
—$(CH_2)_2CO_2CH_3$
—$CH(CH_3)OH$
—$CH(CH_3)OCH_3$
—$CH(CH_3)CHO$
—$CH(CH_3)CO_2H$
—$CH(CH_3)CO_2CH_3$
—$CH(CH_3)CH_2OH$
—$CH(CH_3)CH_2OCH_3$
—$CH(CH_3)CH_2CHO$
—$CH(CH_3)CH_2CO_2H$
—$CH(CH_3)CH_2CO_2CH_3$
—$CH(OH)_2$
—$CH(OH)OCH_3$
—$CH(OH)CHO$
—$CH(OH)CO_2H$
—$CH(OH)CO_2CH_3$
—$CH(OCH_3)OH$
—$CH(OCH_3)_2$
—$CH(OCH_3)CHO$
—$CH(OCH_3)CO_2H$
—$CH(OCH_3)CO_2CH_3$
—$CH(OH)CH_2OH$
—$CH(OH)CH_2OCH_3$
—$CH(OH)CH_2CHO$
—$CH(OH)CH_2CO_2H$
—$CH(OH)CH_2CO_2CH_3$
—$CH(OCH_3)CH_2OH$
—$CH(OCH_3)CH_2OCH_3$
—$CH(OCH_3)CH_2CHO$
—$CH(OCH_3)CH_2CO_2H$
—$CH(OCH_3)CH_2CO_2CH_3$
—$(CH_2)_3OH$
—$(CH_2)_3OCH_3$
—$(CH_2)_3CHO$
—$(CH_2)_3CO_2H$
—$(CH_2)_3CO_2CH_3$
—CHCHOH (cis or trans)
—$CHCHOCH_3$ (cis or trans)
—CHCHCHO (cis or trans)
—$CHCHCO_2H$ (cis or trans)
—$CHCHCO_2CH_3$ (cis or trans)
—$CH_2CHCHOH$ (cis or trans)
—$CH_2CHCHOCH_3$ (cis or trans)
—$CH_2CHCHCHO$ (cis or trans)
—$CH_2CHCHCO_2H$ (cis or trans)
—$CH_2CHCHCO_2CH_3$ (cis or trans)

TABLE 2

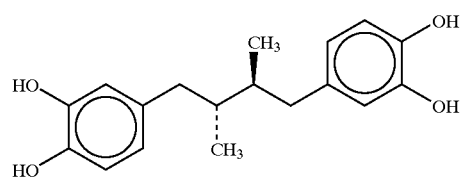

Nordihydroguaiaretic Acid

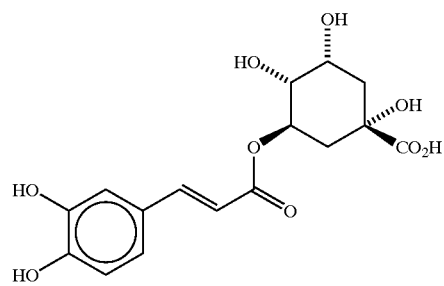

Chlorogenic Acid

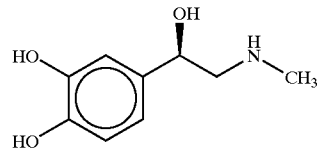

Epinephrine

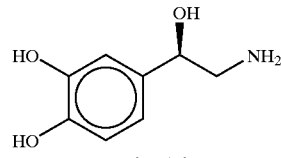

Norepinephrine

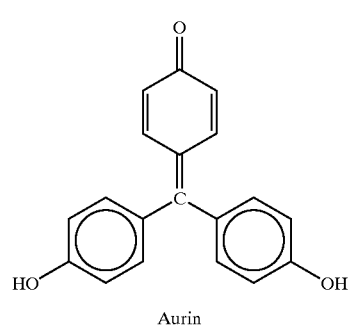

Aurin

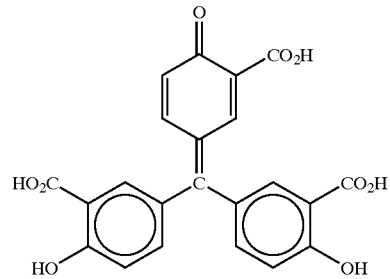

Aurintricarboxylic Acid

TABLE 2-continued

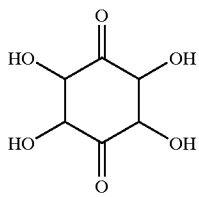

Tetrahydroxybenzoquinone

Various initial concentrations of starting organic compounds in distilled water can be employed and no lower or upper limits are uniformly required. A low concentration solution of sodium hydroxide, such as 0.1 Normal, may also be employed as a diluent for the starting organic compound. The appropriate initial concentration of the starting organic compound or compounds is determined by the synthesis yield requirements and inherent requirements, such as the upper limit of aqueous solubility of the starting organic compound or compounds. Conventional methods are employed to determine the appropriate initial concentration of the starting organic compound or compounds.

The pH of the aqueous solution containing the starting organic compound or compounds can be adjusted in step B) to between about 8 and 11 by adding aqueous ammonium hydroxide, or other aqueous alkaline oxide or hydroxide, or aqueous alkaline earth oxide or hydroxide, or aqueous transition metal oxide or hydroxide. Additionally, if the initial aqueous solution contains a low concentration of base, such as 0.1 Normal sodium hydroxide and the initial solution pH is too high, an acid such as hydrochloric acid may be employed to adjust the pH to the desired value. Other inorganic acids may also be employed for pH adjustment. Note that if hydrochloric acid is employed to adjust the pH downward from an initial high value, care should be taken to avoid letting the pH go below 8. Acidic conditions below pH 7 should be avoided in the presence of hydrochloric acid to eliminate the possibility of formation of mutagenic chlorinated humic acid materials.

An alkaline periodate salt or alkaline earth periodate salt may be employed as an oxidant or polymerization initiator of the starting organic compound in step C). Sodium periodate is particularly preferred. The concentration of the alkaline periodate salt or alkaline earth periodate salt is generally between about 10% and 100% of the starting organic compound or compounds on a molar basis. Thus, if 10 millimoles of starting organic compound is employed, 1 to 10 millimoles of alkaline periodate salt may be employed. Preferably, a molar concentration of periodate that is about 10%–50% of the molar concentration of the starting organic compound or compounds is employed. Most preferably, a molar concentration of periodate that is about 25%–35% of the molar concentration of the starting organic compound or compounds is employed. The exact concentration to be used can be determined by conventional synthetic yield optimization techniques.

Alkaline or alkaline earth sulfides or transition metal sulfides can be optionally added to the initial aqueous solution containing the starting organic compound or compounds following the pH adjustment in step B) and immediately before, at the same time, or following the addition of the periodate in step C). Sulfides contribute to the phenolic polymeric structure, the stability of the structure and its biological activity. Sodium sulfide nonahydrate is a particularly preferred sulfide. The concentration of the sulfide is generally between about 1% and 20% of the starting organic compound or compounds on a molar basis. Thus, if 10 millimoles of starting organic compound is employed, 0.1 to 2 millimoles of sulfide may be employed. Preferably, a molar concentration of sulfide that is about 5%–15% of the molar concentration of the starting organic compound or compounds is employed. Most preferably, a molar concentration of sulfide that is about 8% to 12% of the molar concentration of the starting organic compound or compounds is employed. The exact concentration of sulfide to be used can be determined by conventional synthetic yield optimization techniques.

The pH-adjusted aqueous solution containing the starting organic compound, periodate and optional sulfide is placed in a water-bath or other thermostat heating device at about 20° C. to 100° C. for a period of about 30 minutes to 100 hours in step D). Alternatively, the aqueous solution itself may be thermostated between about 20° C. and 100° C. for a period of about 30 minutes to 100 hours. A preferred temperature and time period is between about 35° C. and 80° C. for about 30 minutes to 100 hours. A particularly preferred temperature and time is about 50° C. for about 30 minutes to two hours. Alternative temperatures and pressures that are equivalent to the above temperature and pressures may be used.

Steps B) and C) above give conditions for oxidizing and polymerizing the starting organic compound. Although the use of periodate salt in basic conditions is preferable, there are other conditions that can perform oxidation and polymerization of the starting organic compound. One may substitute other reagents known in the art that are known to perform this function. If the reagents for oxidation and polymerization are substituted, the temperature and time period for the reaction in step D) should be adjusted accordingly for optimization. For example, a phenolic solution with 2 equivalents of hydrogen peroxide can react for one week at 23° C. to form humic acids.

Following this period, salts are added to the solution resulting from step D) alone or in combination in step E). Salts containing boron, calcium and other alkaline earths, iron and other transition metals are preferred. Such salts may contribute to the phenolic polymeric structure, its stability and biological activity. Boric acid or boron-containing-borate salts, such as sodium borate, are particularly preferred, as are alkaline earth salts, such as calcium sulfate dihydrate, and transition metal salts, such as ferrous sulfate heptahydrate. The concentrations of each of the salts employed is generally between about 0. 1% and 20% of the starting organic compound or compounds on a molar basis. Preferably, a molar concentration of salt which is about 0.2% to 10% of the molar concentration of the starting organic compound or compounds is employed. Most preferably, a molar concentration of salt that is about 0.2% to 2% of the molar concentration of the starting organic compound or compounds, is employed. The exact concentration to be used can be determined by conventional synthetic yield optimization techniques. The solution resulting from step E) is allowed to stand at between about 20° C. and 100° C. with or without stirring for a period of at least 2 hours in step F). Preferably, the solution is allowed to stand at between about 20° C. and 80° C. for about 2 to 48 hours. Alternative temperatures and pressures that are equivalent to the above temperature and pressures may be used. Any precipitate formed at this stage is removed via conventional centrifugation.

Molecules below about 500 to about 10,000 daltons in the solution resulting from step F) are removed in step G). A variety of known conventional techniques can be employed, such as preparative chromatography, ultrafiltration or dialysis. Molecules are preferably removed from the solution resulting from step F) by employing dialysis in step G) with a flow-through open-channel or screen membrane apparatus consisting of a sandwich-type membrane of lower molecular-weight cutoff of 500–10,000 daltons until the conductivity of the solution has dropped to about 200 microsiemens or less. Most preferably, molecules are removed from the solution resulting from step F) by employing dialysis in step G) until the conductivity of the solution has dropped to about 50 microsiemens or less. A Pall Filtron Ultrasette® Tangential Flow Device or Mini-Ultrasette® Tangential Flow Device used with a Pall Filtron Ultralab® Specialized Pump and Reservoir System is preferred for solution dialysis.

The conductivity of the solution processed in step G) above can conveniently be monitored with a flow-through conductivity cell and conductivity meter. Alternatively, a simple inexpensive hand-held combination conductivity cell/conductivity meter (e.g., a Nalcometer Model MLN) can be employed.

Before removing the water from the above solution in step H), the solution resulting from step G) above can be further dialyzed with a flow-through apparatus consisting of a sandwich-type membrane of molecular weight cutoff of 50,000 daltons. In this case, the filtrate solution, not the retentate, is saved for further concentrating and processing according to steps H) and I). The resultant product will have a molecular-weight range of 500–50,000 daltons.

If the solution resulting from either steps G) or H) above is to be stored as an aqueous solution for long periods of time for later application or use, for example as an anti-viral treatment solution, anti-viral therapy, anti-microbial therapy, a spray-on fertilizer or soil amendment, it can be filtered through standard 0.2–0.4 micron filters to remove bacteria and viruses, that is, can be made sterile by filtration. Alternatively, the aqueous solution from either steps G) or H) can be autoclaved for about 5–60 minutes at about 100–150° C. to produce a sterile solution.

A final optional step I) in the process involves removing water from the solution resulting from step H). When freeze-drying is employed as the method of water removal in step I) above, the resultant product is a light fluffy dark-colored powder that is subject to static electricity effects. To minimize these effects, a small amount of mannose or other sugar can be added to the solution resulting from step H) just prior to freeze-drying. Water removal from the product can be carried out by means other than freeze-drying in step I) above, such as by heat evaporation with or without vacuum, by rotary evaporation, by spray-drying, or by any other solvent-removal technique that is convenient as well as economical for aqueous solutions. The dried powder obtained from step I) above can be autoclaved for about 15–30 minutes at about 100–120° C. to produce a sterile powder.

The synthetic humic acid materials produced according to the chemical processes and separation and isolation procedures of the preferred embodiments exhibit the physico-chemical properties and attributes of typical naturally-occurring commercially-available humic acids and other soil extracts.

A facile method of examining the physicochemical characteristics of the product yielded by steps A) through H) above, or by modifications thereto, is high performance liquid chromatography (HPLC). The chromatographic fingerprint pattern so obtained from HPLC also offers a convenient means of comparing one product with another, as well as comparing each of the synthetic products with naturally-occurring humic acids and other soil-extract materials. The HPLC method is thus used to determine the reproducibility of the physiochemical properties and attributes of the synthetic phenolic polymeric materials, as well as to determine if the aforementioned properties and attributes simulate the physiochemical properties and attributes of typical commercial-available natural humic acids and other soil extracts. The latter determination of simulation is done in the conventional manner employing HPLC; e.g., by visually and quantitatively comparing the HPLC chromatographic fingerprint patterns of the materials. The fingerprint patterns of the two materials, one synthetic and one natural, need not be 100% identical to conclude that the physiochemical properties and attributes of the synthetic phenolic polymeric material simulates the physiochemical properties and attributes of the natural humic acid. An approximate correspondence between the aforementioned HPLC fingerprint patterns is all that is required to conclude that the synthetic material simulates the natural material. In general, even a 75% visual correspondence in two HPLC fingerprint patterns is all that is necessary to conclude that one material simulates another.

A useful fingerprint pattern for natural as well as synthetic soil extract materials can be obtained as follows. The column comprises packing, typically reversed-phase polymer PRP-1 (Hamilton Co.), of particle size 5 microns, and being 150 millimeters in length by 4.1 millimeters inside diameter. The mobile phase comprises three solutions: Solution A, Solution B, and Solution C. Solution A is 0.1 Normal aqueous sodium hydroxide. Solution B is 0.05 Normal of so-called Prideaux universal buffer, which is made by combining 4.25 grams of sodium nitrate ($NaNO_3$), 12.37 grams of boric acid ($H_3BO_3$), 23.06 grams of phosphoric acid ($H_3PO_4$), and 12.01 grams of acetic acid ($CH_3CO_2H$) with 4 liters of distilled water. Solution C is 100% methanol ($CH_3OH$). The mobile-phase gradient employed for an HPLC run consists of 40% solution A plus 60% solution B at the beginning, which composition is changed in a linear manner to 100% solution A after 20 minutes. The mobile phase is then changed linearly again to 10% A plus 90% C over the next 5 minutes, which final composition is held for the purpose of a column wash for the next 35 minutes. The mobile-phase flow rate is 1 milliliter per minute. The detector is Uv-Visible, which is set at 340 nanometers. The chart speed is typically 0.5 centimeter per minute. The sample loop size is 5–20 microliters. Solutions are prepared for HPLC by dissolving 0.1–10 grams of dried sample in 100 milliliters of distilled water or 0.1 Normal aqueous sodium hydroxide of pH 8–10.

The chemical processes and separation and isolation procedures of the preferred embodiments are suitable for scale-up directly to industrial levels that provide economically acceptable yields. The chemical processes and separation and isolation procedures of the preferred embodiments can produce synthetic product yields approaching 100%. More typically, about 0.08 to 0.65 g of synthetic humic acid can be produced from about 10 millimoles of starting organic compound or compounds in 300 milliliters. These procedures can be scaled up to pharmaceutical production scales employing about 10,000 to 20,000 liters or more of initial solution containing the starting organic compound or compounds. A total yield between about 2.7 and 21.7 kilograms of synthetic humic acid can be achieved utilizing a 10,000-liter thermally-jacketed stainless-steel tank and a concentration of starting organic compound of about 10 millimoles per 300 milliliters. A single anti-viral treatment may employ milligram amounts of synthetic humic acid. Twenty kilograms of synthetic humic acid represents 2 million units of anti-viral product at 10 milligrams per unit. Even at a treatment cost of $0.10 per unit, this amount represents $200,000.00 of synthetic humic acid. Since the starting organic compounds utilized in the preferred embodiments are relatively inexpensive, the synthesis yields of the chemical processes and separation and isolation procedures are economically very acceptable.

Examples 1 through 9 are illustrative of the variety of starting organic compounds that can be employed in the process of the preferred embodiments. It was not considered necessary to carry out all steps of the process to illustrate starting compound variety. More particularly, Examples 1 through 9 are illustrative of all steps of the process with the exception of step E), the addition of salts.

EXAMPLE 1

Preparation of a Synthic Humic Acid from 25-Dihydroxybenzoic Acid (Gentisic Acid)

The starting organic compound is 2, 5-dihydroxybenzoic acid (gentisic acid), shown in Table 1, represented by $R_1$=—$CO_2H$, $R_2,R_5$=—OH, and $R_3,R_4,R_6$=—H Gentisic acid (1.55 grams, 10 mmoles) was dissolved in 300 milliliters of 0.1 N aqueous sodium hydroxide (NaOH). The solution pH was adjusted to 8.5 with 6 N HCl. Sodium periodate (0.54 gram, 2.5 mmoles) was added, and the solution was placed in a water-bath at 50° C. for 30 minutes. The solution was allowed to stand at room temperature overnight. Any precipitate was removed by centrifugation. The solution was dialyzed with a 1,000-dalton cut-off flow-through open-channel or screen membrane system (Pall Filtron: Ultrasette® 7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Five to twenty hundredths of a gram of mannose or other suitable carbohydrate can be added to the solution prior to freeze-drying to reduce static electricity effects associated with the freeze-dried powder.) The yield of synthetic soil extract was 0.2 gram.

The following Examples 2–9 employ the synthesis procedure of Example 1 beginning with the adjustment of solution pH.

EXAMPLE 2

Preparation of a Synthetic Humic Acid from 3,4-Dihydroxyphenylacetic Acid (Homoprotocatechuic Acid)

The starting organic compound is 3,4-dihydroxyphenylacetic acid (homoprotocatechuic acid), shown in Table 1, represented by $R_1$=—$CH_2CO_2H$, $R_3,R_4$=—OH, and $R_2,R_5,R_6$=—H. Homoprotocatechuic acid (1.68 grams, 10 mmoles) was dissolved in 300 milliliters of 0.1 N aqueous sodium hydroxide (NaOH). The remaining procedure followed that of Example 1. The yield of synthetic soil extract was 0.24 gram.

EXAMPLE 3

Preparation of a Synthetic Humic Acid from Dl-(3 4-Dihydroxyphenyl)Hydroxyacetic Acid Dl-3,4-Dihydroxymandelic Acid)

The starting organic compound is dl-(3, 4-dihydroxyphenyl)hydroxyacetic acid (dl-3,4-dihydroxymandelic acid), shown in Table 1, represented by $R_1$=—CH(OH)$CO_2H$, $R_3,R_4$=—OH, and $R_2,R_5,R_6$=—H. dl-3,4-Dihydroxymandelic acid (1.68 grams, 10 mmole was dissolved in 300 milliliters of 0.1 N aqueous sodium hydroxide (NaOH). The remaining procedure followed that of Example 1. The yield of synthetic soil extract was 0.08 gram.

EXAMPLE 4

Preparation of a Synthetic Humic Acid from Aurintricarboxylic Acid

The starting organic compound is aurintricarboxylic acid, shown in Table 2. Aurintricarboxylic acid (4.2 grams, 10 mmoles) was dissolved in 300 milliliters of 0.1 N aqueous sodium hydroxide (NaOH). The remaining procedure followed that of Example 1. The yield of synthetic soil extract was 4.7 grams.

EXAMPLE 5

Preparation of a Synthetic Humic Acid from 3-(3.4-Dihydroxyphenyl)Propenic Acid (Caffeic Acid)

The starting organic compound is 3-(3,4-dihydroxyphenyl)propenoic acid (caffeic acid), shown in Table 1, represented by $R_1$=—$CHCHCO_2H$, $R_3,R_4$=—OH, and $R_2,R_5,R_6$=—H. Caffeic acid (1.80 grams, 10 mmoles) was dissolved in 300 milliliters of 0.1 N aqueous sodium hydroxide (NaOH). The remaining procedure followed that of Example 1. The yield of synthetic soil extract was 0.65 gram.

EXAMPLE 6

Preparation of a Synthetic Humic Acid from Tetrahydroxybenzoquinone

The starting organic compound is tetrahydroxybenzoquinone, shown in Table 2. Tetrahydroxybenzoquinone (1.72 grams, 10 mmoles) was dissolved in 300 milliliters of 0.1 N aqueous sodium hydroxide (NaOH). The remaining procedure followed that of Example 1. The yield of synthetic soil extract was 0.016 gram.

EXAMPLE 7

Preparation of a Synthetic Humic Acid from 1,4-Dihydroxybenzene (Hydroquinone)

The starting organic compound is 1, 4-dihydroxybenzene (hydroquinone), shown in Table 1, represented by $R_1,R_4$=—OH, and $R_2,R_3,R_5,R_6$=—H. Hydroquinone (1.10 grams, 10 numoles) was dissolved in 300 milliliters of 0.1 N aqueous sodium hydroxide (NaOH). The remaining procedure followed that of Example 1. The yield of synthetic soil extract was 0.16 gram.

EXAMPLE 8

Preparation of a Synthetic Humic Acid from 3,4,5-Trihydroxybenzenoic Acid (Gallic Acid)

The starting organic compound is 3,4,5-trihydroxybenzenoic acid (gallic acid), shown in Table 1, represented by $R_1$=—$CH_2CO_2H$, $R_3,R_4,R_5$=—OH, and $R_2,R_6$=—H. Gallic acid (1.70 grams, 10 mmoles) was dissolved in 300 milliliters of 0.1 N aqueous sodium hydroxide (NaOH). The remaining procedure followed that of Example 1. The yield of synthetic soil extract was 0.10 gram.

EXAMPLE 9

Preparation of a Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid was (1.68 grams, 10 mmoles) dissolved in 300 milliliters of 0.1 N aqueous sodium hydroxide (NaOH). The remaining procedure followed that of Example 1. The yield of synthetic soil extract was 0.20 gram.

The following Examples 10–14 are illustrative of a process of the preferred embodiments including step E), addition of salts. Addition of salts increases the activity of the synthetic humic acids produced by the method. Examples 10–14 illustrate that the synthetic humic acid materials produced according to the chemical processes and separation and isolation procedures of the preferred embodiments exhibit the physicochemical properties and attributes of typical naturally-occurring commercially-available humic acids and other soil extracts. Examples 10–14 also illustrate that the therapeutic indications of the synthetic humic acids produced according to the chemical processes and separation and isolation procedures of the preferred embodiments are those of soil extracts and humic acids in general, that is to say for viral-related disorders and diseases.

EXAMPLE 10

Preparation of Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid (1 gram, 6 nimoles) was dissolved in 300 milliliters of 0.1 N aqueous sodium hydroxide (NaOH). The solution pH was adjusted to 8.5 with 6 N HCl. Sodium periodate (0.32 gram, 1.5 mmoles) and sodium sulfide nonahydrate (0.12 gram, 0.5 millimole) was added, and the solution was placed in a water bath at 50° C. overnight. Boric acid (0.001 gram, 0.016 millimole), ferrous sulfate heptahydrate (0.021 gram, 0.075 millimole), and calcium sulfate dihydrate (0.006 gram, 0.035 millimole) were added and the solution was stirred for 2 hours at room temperature. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.23 gram.

Figure 2:
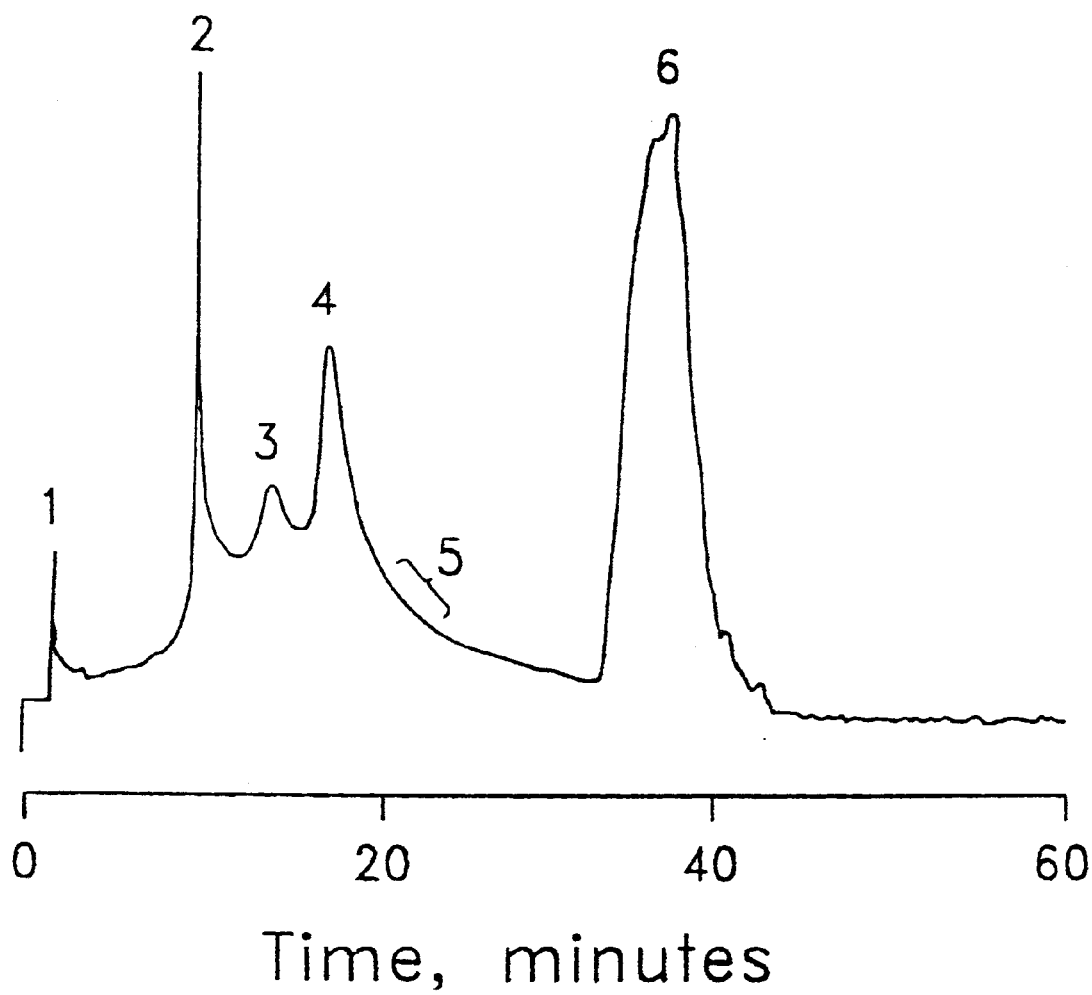
FIG. 2 shows a high-performance liquid chromatography (HPLC) trace obtained for a typical commercially-available natural-product humic acid.

The HPLC trace of the synthetic soil extract obtained in Example 10 is illustrated in FIG. 1. Peaks 1–6 were produced by this example. Peak 5 is under the shoulder of Peak 4 and is not overtly apparent. A mathematical first derivative of the detector signal versus time can more clearly show Peak 5. FIG. 2 shows the HPLC trace of a typical commercially-available natural humic acid. Peak 6 in FIGS. 1 and 2 was produced by a column wash with 90–100% v/v methanol and also contains synthetic humic acid. It can be seen that with the exception of the relative amounts of material in Peaks 2, 4, and 6, the remainder of the HPLC traces in FIGS. 1 and 2 are similar. Thus, the synthetic procedure of the preferred embodiments produced a humic acid material with physicochemical characteristics that are similar to those of a commercially available soil extract.

EXAMPLE 11

Preparation of Synthetic Humic Acid from 2,5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid (1.68 grams, 10 mmoles) was dissolved in 300 milliliters of 0.1 N aqueous sodium hydroxide (NaOH). The solution pH was adjusted to 8.5 with 6 N HCl. Sodium periodate (0.75 gram, 3.5 mmoles) and sodium sulfide nonahydrate (0.24 gram, 1 millimole) was added, and the solution was placed in a water bath at 50° C. overnight. Boric acid (0.006 gram, 0.1 millimole), ferrous sulfate heptahydrate (0.28 gram, 1 millimole), and calcium sulfate dihydrate (0.17 gram, 0.1 millimole) were added and the solution was stirred for 48 hours at room temperature. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.47 gram. The HPLC trace of the synthetic soil extract obtained in Example 11 was similar to that described in Example 10 and illustrated in FIG. 1.

EXAMPLE 12

Preparation of Synthetic Humic Acid from 2.5-Dihydroxyphenylacetic Acid (Homogentisic Acid)

The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. The starting organic compound is 2,5-dihydroxyphenylacetic acid (homogentisic acid), shown in Table 1, represented by $R_1$=—$CH_2CO_2H$, $R_2,R_5$=—OH, and $R_3,R_4,R_6$=—H. Homogentisic acid (1.68 grams, 10 mmoles) was dissolved in 300 milliliters of 0.1 N aqueous sodium hydroxide (NaOH). The solution pH was adjusted to 8.5 with 6 N HCl. Sodium periodate (0.75 gram, 3.5 mmoles) and sodium sulfide nonahydrate (0.24 gram, 1 millimole) was added, and the solution was placed in a water bath at 50° C. overnight. Boric acid (0.006 gram, 0.1 millimole), ferrous sulfate heptahydrate (0.28 gram, 1 millimole), and calcium sulfate dihydrate (0.17 gram, 0.1 millimole) were added and the solution stood quiescent overnight at 50° C. Any precipitate was removed by centrifugation. The solution was dialyzed with a 1,000-dalton cut-off flow-through open-channel or screen membrane system (Pall Filtron: Ultrasette®7 Tangential Flow Device or Mini-Ultrasette® 7 Tangential Flow Device used with a Pall Filtron Ultralab® 7 Specialized Pump and Reservoir System) to a conductivity of 30 microsiemens or less against distilled water. The dialysis apparatus was then used to concentrate the solution to about 200 milliliters. The solution can be saved at this point for further use as an aqueous solution; or it can be freeze-dried to a powder. (Fifty to two hundred milligrams of mannose or other suitable carbohydrate can be added to the solution prior to freeze-drying to reduce static electricity effects associated with the freeze-dried powder.) The yield of synthetic soil extract was 0.4 gram. The HPLC trace of the synthetic soil extract obtained in Example 12 was similar to that described in Example I 0 and illustrated in FIG. 1.

EXAMPLE 13

Preparation of Synthetic Hiumic Acid from 3,4-Dihydroxycinnamic Acid (Caffeic Acid)

The starting organic compound is 3,4-dihydroxycinnamic acid (caffeic acid), shown in Table 1, represented by $R_1$=—CHCHCO$_2$H, $R_3,R_4$=—OH, and $R_2,R_5,R_6$=—H. Caffeic acid (1.8 grams, 10 mmoles) was dissolved in 300 milliliters of 0.1 N aqueous sodium hydroxide (NaOH). The remaining procedure followed that of the preceding Example. The yield of synthetic soil extract was 0.51 gram.

EXAMPLE 14

Preparation of a Synthetic Humic Acid from 1,3,4,5-Tetrahydroxycyclohexane-Carboxylic Acid 3-(3.4-Dihydroxycinnamate) (Chlorogenic Acid)

The starting organic compound is 1,3,4,5-tetrahydroxycyclohexane-carboxylic acid 3-(3,4-dihydroxycinnamate) (chlorogenic acid), shown in Table 2. Chlorogenic acid (3.54 grams, 10 mmoles) was dissolved in 300 milliliters of 0.1 N aqueous sodium hydroxide (NaOH). The remaining procedure followed that of the preceding Example. The yield of synthetic soil extract was 0.23 gram.

EXAMPLE 15

In Vitro Toxicity of Synthetic Humic Acid prepared according to Examples 10. 11. and 12

Humic acid synthesized from homogentisic acid was prepared according to the procedure of Examples 10, 11 and 12. The in vitro toxicity of the materials was assessed as follows:

Five units of 450 milliliters each of whole human blood were collected into CP2D/AS-3 Leukotrap RC-PL systems. The blood was rested for 3 hours at room temperature. Each sample was weighed, and then centrifuged at 2820 revolutions per minute (2312 gravities) for 3 minutes, 44 seconds. The blood samples were then expressed through ATS-LPL filters into platelet storage bags. The filtration time was noted. The LR-PRP was centrifuged at 3600 revolutions per minute (3768 gravities) for 7 minutes. All but about 55 grams of platelet poor plasma was removed from each sample. The platelet concentrates were rested for 90 minutes at room temperature, and were then weighed and placed in a platelet incubator. RCM1 filters were primed with AS-3 solution. The primary bags were hung at a height of 60 inches above empty AS-3 bags, such that filtration occurred by gravity. The filtration time was noted, and the LRRCC systems were sealed off 3 inches below the RCM1 filters. Each RCM1 filter together with 6 inches of tubing and the LR-RCC, including the donor identification tube segment, were weighed. Samples were taken at this point for post-filtration testing (LR-RCC).

At Day 1, sufficient synthetic humic acid was added to each platelet concentrate so as to make its concentration 25 micrograms per milliliter. Treated platelet concentrates were then incubated in a platelet incubator for 1 hour, following which samples of each platelet concentrate were taken for testing. Subsequent samples were also taken on Day 5 for further testing.

Table 3 shows the effect of the synthetic humic acid prepared as described in Example 10 on the viability of platelet concentrates as measured according to the procedures of this Example. The results were all nominal, that is, the synthetic humic acid had no effect on platelet viability (i.e., is nontoxic). The same results were obtained when the concentration of humic acid was made 100 micrograms per milliliter instead of 25 micrograms per milliliter. These results are particularly noteworthy, as blood platelets are known to be sensitive to a variety of chemical agents. It is for this reason that few safe antiviral treatments are available for blood platelets.

TABLE 3

| Unit No. | pH at 22° C. | | pCO$_2$, mm Hg | | pO$_2$, mm Hg | | HCO3, mmol/L | | MPV, fl | |
|---|---|---|---|---|---|---|---|---|---|---|
| | Day 1 | Day 5 | Day 1 | Day 5 | Day 1 | Day 5 | Day 1 | Day 5 | Day 1 | Day 5 |
| 1 | 7.466 | 7.394 | 19.3 | 12.8 | 33.5 | 44.4 | 16.8 | 9.5 | 7.0 | 6.6 |
| 2 | 7.321 | 7.215 | 21.6 | 14.3 | 9.9 | 22.2 | 13.8 | 7.3 | 6.7 | 6.3 |
| 3 | 7.320 | 7.276 | 24.4 | 16.6 | 10.3 | 21.3 | 15.6 | 9.7 | 6.7 | 6.5 |
| 4 | 7.368 | 7.308 | 20.7 | 14.3 | 13.4 | 22.2 | 14.6 | 8.9 | 6.5 | 6.3 |
| 5 | 7.457 | 7.454 | 20.1 | 13.8 | 23.7 | 29.0 | 17.1 | 11.6 | 7.7 | 7.4 |
| Mean | 7.386 | 7.329 | 21.2 | 14.4 | 18.2 | 27.8 | 15.6 | 9.4 | 6.9 | 6.6 |
| Std. Dev. | 0.071 | 0.095 | 2.0 | 1.4 | 10.2 | 9.8 | 1.4 | 1.5 | 0.5 | 0.6 |

TABLE 3-continued

| Unit No. | WBC Yield, × 10⁵ Day 1 | Platelet Yield, × 10¹⁰ | | Streaming | | % ESC | | % HSR | | Lactate, mmol/L | |
|---|---|---|---|---|---|---|---|---|---|---|---|
| | | Day 1 | Day 5 | Day 1 | Day 5 | Day 1 | Day 5 | Day 1 | Day 5 | Day 1 | Day 5 |
| 1 | 0.1 | 8.3 | 9.0 | 3 | 3 | 24.2 | 16.9 | 78.0 | 64.0 | 5.1 | 12.1 |
| 2 | 0.2 | 14.5 | 14.2 | 3 | 3 | 27.5 | 20.3 | 81.7 | 71.5 | 6.6 | 13.4 |
| 3 | 0.4 | 13.3 | 13.4 | 3 | 3 | 28.7 | 26.3 | 81.7 | 79.4 | 6.3 | 12.4 |
| 4 | 0.3 | 11.7 | 12.3 | 3 | 2 | 22.1 | 19.2 | 81.4 | 77.1 | 6.6 | 13.1 |
| 5 | 0.3 | 8.9 | 9.1 | 3 | 3 | 19.1 | 14.4 | 74.7 | 70.2 | 4.5 | 9.7 |
| Mean | 0.3 | 11.3 | 11.6 | 3.0 | 2.8 | 24.3 | 19.4 | 79.5 | 72.4 | 5.8 | 12.1 |
| Std. Dev. | 0.1 | 2.7 | 2.4 | 0.0 | 0.4 | 3.9 | 4.5 | 3.1 | 6.1 | 1.0 | 1.4 |

EXAMPLE 16

In Vitro Toxicity of Synthetic Humic Acid prepared accordint to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The in vitro toxicity of the materials was assessed as follows:

Cytotoxicity was examined with six concentrations of each humate material, and one "no-drug" concentration. All materials were tested in African green monkey kidney cells (CV-1; Diagnostic Hybrids, Inc., Athens, Ga.) in triplicate. The cells were provided in flat dishes containing multiple cell wells. The cells were cultured in the presence of different concentrations of humate materials for 24–36 hours at 35–37° C. in a $CO_2$-humidified incubator. The morphology of the cultured cells was examined visually to determine any cytotoxic effects. No abnormal cell morphology was observed in cultures with "no drug"nor in any containing humate concentrations up to 500 micrograms per milliliter. Furthermore, no apparent CV-1 cell death (that is, cell detachment from the bottom of the wells) was observed at any concentration of any material tested. The results established that the materials were not cytotoxic at concentrations up to at least 500 micrograms per milliliter.

EXAMPLE 17

In Vitro Toxicity testing of Synthetic Humic Acid prepared according to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14. The in vitro toxicity of the materials was assessed as follows:

The Neutral Red method of assaying for humate toxicity was carried out in roughly the same manner for all cell lines tested; that employed for human foreskin fibroblast (HFF) cells is provided as a representative example. Twenty-four hours prior to assay, HFF cells were plated into 96-well plates at a concentration of $2.5 \times 10^4$ cells per well. After 24 hours, the medium was aspirated and 125 microliters of medium+humate was added to the first row of wells and then diluted serially 1:5 using the Cetus Liquid Handling System. After humate addition, the plates were incubated for seven days in a $CO_2$ incubator at 37° C. At this time the medium+humate was aspirated and 200 microliters per well of 0.01% neutral red in PBS was added. This was incubated in the $CO_2$ incubator for 1 hour. The dye was aspirated and the cells were washed using a Nunc Plate Washer. After removing the PBS, 200 micrograms per well of 50% EtOH/1% glacial acetic acid (in $H_2O$) was added. The plates were rotated for 15 minutes and the optical densities were read at 540 nanometers on a plate reader.

Visual observation was employed to confirm cell toxicity. Wells of uninfected cells treated with each concentration of test compound were used. The cells were examined microscopically for any changes in appearance compared to normal control cells run in the same plate. These changes became manifest as enlargement, granularity, cells with ragged edges, a filmy appearance, rounding, detachment from the surface of the well, or other changes. The changes were given a designation of T (100% toxic), PVH (partially toxic-very heavy-80%), PH (partially toxic-heavy-60%), P (partially toxic-40%), Ps (partially toxic-slight-20%), or 0 (no toxicity-0%), conforming to the degree of cytotoxicity seen. A 50% cytotoxic concentration ($TC_{50}$) was determined by regression analysis of these data.

All humates evaluated were not cytotoxic at levels at least as high as 100 micrograms per milliliter, as shown below in Table 4. Visual observation of caffeic acid and natural-product humates with uninfected MDCK cells in toxicity control wells appeared initially to indicate drug toxicity. However, the humates were not in fact toxic as revealed by Neutral Red assays. Rather, the humate compounds were found to bind to cell surfaces, thereby changing their color and giving them an exanimate appearance. This discoloration was also observed in a concentration-dependent manner at levels where antiviral activity was present.

TABLE 4

| | $TC_{50}$ | | | | | |
|---|---|---|---|---|---|---|
| | | | | LLC-MK₂[5] | | |
| Compound[1] | BSC-1[2] | HFF[3] | MDCK[4] | Trial 1 | Trial 2a[7] | Trial 2b[8] |
| Caffeic Acid Humate | >100 | >100 | >100 | >100 | >1000 | >1000 |

TABLE 4-continued

| | | | | TC$_{50}$ | | |
| --- | --- | --- | --- | --- | --- | --- |
| | | | | | LLC-MK$_2$[5] | |
| Compound[1] | BSC-1[2] | HFF[3] | MDCK[4] | Trial 1 | Trial 2a[7] | Trial 2b[8] |
| Chlorogenic Acid Humate | >100 | >100 | —[6] | —[6] | >1000 | >1000 |
| Homogentisic Acid Humate | >100 | >100 | >100 | >100 | >1000 | >1000 |
| Natural-Product Humate | >100 | >100 | —[6] | —[6] | 700 | >1000 |

[1]All concentrations in micrograms per milliliter.
[2]African green monkey kidney cells.
[3]Human foreskin fibroblast cells.
[4]Madin Darby canine kidney cells.
[5]Adult rhesus monkey kidney cells.
[6]Not evaluated.
[7]Neutral Red assay.
[8]Visual assay.

EXAMPLE 18

Cell Proliferation (Viaability) Testing of Synthetic Humic Acid prepared according to Example 10–14

Humic acid synthesized from homogentisic acid was prepared according to the procedure of Examples 10–12. Humic acid synthesized from caffeic acid was prepared according to the procedure of Example 13. Humic acid synthesized from chiorogenic acid was prepared according to the procedure of Example 14. Natural-product humic acid was prepared by dialysis with subsequent freeze-drying as described in Examples 1–14.

The in vitro toxicity of the materials in terms of cell proliferation (viability) was assessed in the following procedure. The counting method of assaying for cell proliferation (viability) was carried out in roughly the same manner for all cell lines tested; that employed for HFF cells is provided as a representative example. Twenty-four hours prior to assay, HFF cells were seeded in 6-well plates at a concentration of $2.5 \times 10^4$ cells per well in minimum essential medium (MEM) containing 10% fetal bovine serum (FBS). On the day of the assay, humates were diluted serially in MEM containing 10% FBS at increments of 1:5 covering a range from 100 to 0.03 micrograms per milliliter. The medium from the wells was then aspirated and 2 milliliters of each humate concentration was then added to each well. The cells were then incubated in a $CO_2$ incubator at 37° C. for 72 hours. At the end of this time, the medium+humate solution was removed and the cells washed. One milliliter of 0.25% trypsin was added to each well and incubated until the cells started to come off of the plate. The cell-medium mixture was then pipetted up and down vigorously to break up the cell suspension and 0.2 milliliter of the mixture was added to 9.8 milliliters of Isoton III and counted using a Coulter Counter. Each sample was counted three times with two replicate wells per sample.

All humates except for caffeic acid humate with Daudi cells (Burkitt's lymphoma derived cells) did not inhibit 50% cell proliferation (CP$_{50}$) at drug levels at least as high as 50 micrograms per milliliter, as shown below in Table 5.

TABLE 5

| | CP$_{50}$, µg/mL | |
| --- | --- | --- |
| Compound[1] | HFF[2] | Daudi[3] |
| Caffeic Acid Humate | 71.2 | <0.08 |
| Chlorogenic Acid Humate | 96 | >50 |
| Homogentisic Acid Humate | 88.4 | >50 |
| Natural-Product Humate | >100 | >50 |

[1]All concentrations in micrograms per milliliter.
[2]Human foreskin fibroblast cells.
[3]Burkitt's lymphoma derived cells.

EXAMPLE 19

In Vivo Toxicity of Synthetic Humic Acid prepared according to Examples 10–14

Humic acid synthesized from homogentisic acid was prepared according to the procedure of Examples 10–12. Humic acid synthesized from caffeic acid was prepared according to the procedure of Example 13. Humic acid synthesized from chlorogenic acid was prepared according to the procedure of Example 14. Natural-product humic acid was prepared by dialysis with subsequent freeze-drying as described in Examples 1–14.

The in vivo acute intravenous systemic toxicity of the humate materials was assessed as follows. Each humate material was dissolved separately in sterile, pyrogen-free 0.9% aqueous sodium chloride solvent to yield solutions of final concentrations of 1, 0.5 and 0.25 milligrams per milliliter. The test animals were viral antibody-free Swiss Webster mice, which weighed in the range of 17–23 grams at the time of testing. All test animals were quarantined and checked for signs of disease prior to testing. All test animals were group-housed five per cage in plastic cages with stainless steel suspended lids. For each dose of each humate material, ten mice (five males and five females) were administered the sample humate material intravenously in the amount of 50 milliliters per kilogram body weight. Ten additional mice were similarly administered 0.9% sodium chloride solution (the solvent vehicle) as a zero control. This procedure resulted in humate doses of 50 milligrams per kilogram body weight from the I milligram per milliliter solution, 25 milligrams per kilogram from the 0.5 milligram per milliliter solution, 12.5 milligrams per kilogram from the 0.25 milligram per milliliter solution, and 0 milligrams per kilogram from the 0.9% sodium chloride (blank) solution. Following injection, the mice were offered a balanced Teklad diet and water ad libitum for the duration of the study. All mice were examined for viability for fouteen days. Zero time, Day seven and Day fourteen weights and toxic symptoms were recorded. No mortalities were observed for any of the mice over the fourteen day observation period and, while some clinical findings were observed, they were not indicative of toxicity.

EXAMPLE 20

Anti-Viral properties of Synthetic Humic Acid prepared according to Examples10–11

Several hundred milligrams of synthetic humic acid were prepared according to the procedures of Examples 10 and 11. The anti-viral properties of these materials were assessed according to the following methods:

Jurkat cells obtained from the American Type Culture Collection (Rockville, Md.) were subcultured every fifth day using RPMI-1640 medium supplemented with 2 millimolar L-glutamine and 15 percent by volume fetal bovine serum (FBS). Cell counts were determined with a Coulter particle counter (Coulter Corporation, Hialeah, Fla.). The cells were infected with an HIV-1 plasmid construct, pNL4-3 (A. Adachi, H. E. Gendleman, S. Koenig, T. Folks, R. Willey, A. Rabson, and M. A. Martin, *J. Virol.* 1986, 59, 284–291). Cell cultures thereby treated produce high levels of HIV-1, approximately $1 \times 10^7$ particles per milliliter, as measured by electron microscopy. The infected cells were then cultured in complete medium containing RPMI-1640 supplemented with 2 millimolar L-glutamine, 15 percent by volume fetal calf serum, and 1 percent by volume Pen-Strep (100 Units of Penicillin and 100 milligrams of Streptomycin per milliliter). The cells were monitored for approximately four weeks prior to use in order to ensure stable HIV-1 production.

Prior to testing the anti-viral efficacy of synthetic humic acid, the Jurkat cell culture supernatants were first tested for HIV-1 p24 production to establish a pretreatment baseline. After confirming the level of virus production, the growth medium was changed and the cell number was adjusted to $1.5 \times 10^6$ cells per milliliter. Then, two days prior to administering the synthetic humic acid to be tested, equal volumes of transfected cells were admixed with normal, untreated cells to bring the level of virus production to within the range of the HIV-1 p24 immunoassay. After 24 hours, a known quantity of synthetic humic acid was added to the cell blend. The determination of HIV-1 p24 expression after a given number of days following synthetic humic acid administration was carried out with a solid-phase assay designed for HIV-1 antigens (HIVAG-1; Abbott Laboratories, Diagnostic Division, Abbott Park, Illinois; Abbott Quantum II ELISA reader and data reduction module 1.21).

Figure 3:
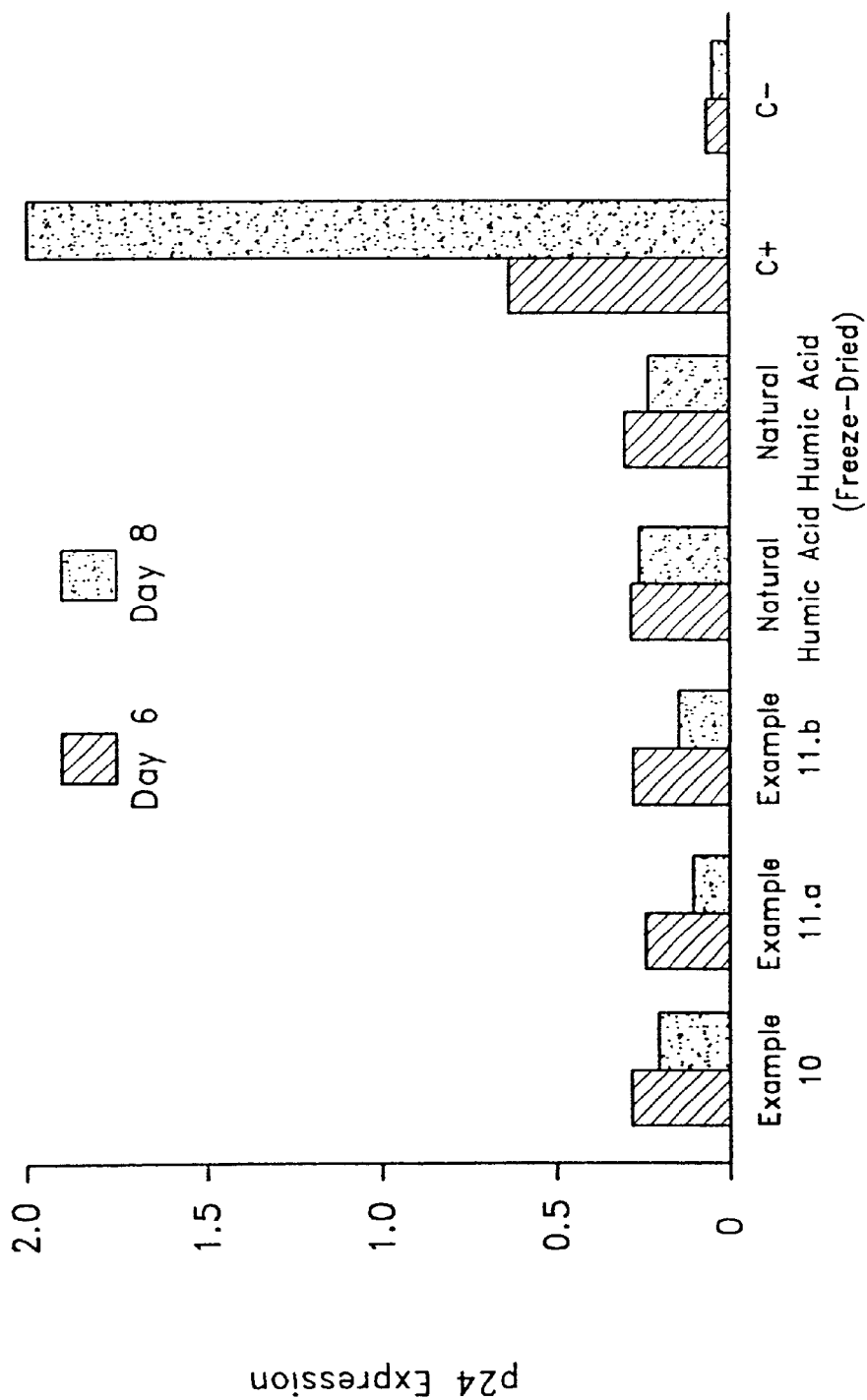
FIG. 3 shows a bar graph of the p24 expression of HIV-positive cells harvested 6 and 8 days after treatment with synthetic humic acids prepared as described in Examples 10 and 11 together with comparative results obtained for natural-product humic acid that had been dialyzed, and natural-product humic acid that had been dialyzed and freeze-dried.

FIG. 3 shows the effect of the synthetic humic acid prepared as described in Examples 10 and 11 on the p24 expression of HIV-positive cells as measured according to the procedures of Example 20. Example 11a in FIG. 3 was prepared exactly according to the procedure of Example 11. Example 11b in FIG. 3 was prepared according to the procedure of Example 11 with the additional step of freeze-drying the final solution. Shown for comparison are the results obtained with natural-product humic acid that was subjected to dialysis as described in Examples 1–11; and natural-product humic acid that was subjected to dialysis with subsequent freeze-drying as described in Examples 1–11. C+ and C– are positive and negative controls, respectively. The results show significant reductions in p24 expression for all samples which contained humic acids. Additionally, at day 12, no p24 was detected within the experimental error of the method (none greater than the C-control).

EXAMPLE 21

HIV Cytoprotection Properties of Natural-Product and Synthetic Humic Acids prepared according to Examples 9. 10. AND 11

Several hundred milligrams of synthetic humic acid were prepared according to the procedures of Examples 9, 10, and 11. Synthetic humic acid (no salts) was prepared as described in Example 9. Synthetic humic acid (salts-I) was prepared as described in Example 10. Synthetic humic acid (salts-II) was prepared as described in Example 11. Natural-product humic acid was prepared by dialysis with subsequent freeze-drying as described in Examples 1–11. The anti-viral properties of these materials were assessed according to the methods described in Example 20.

Figure 4:
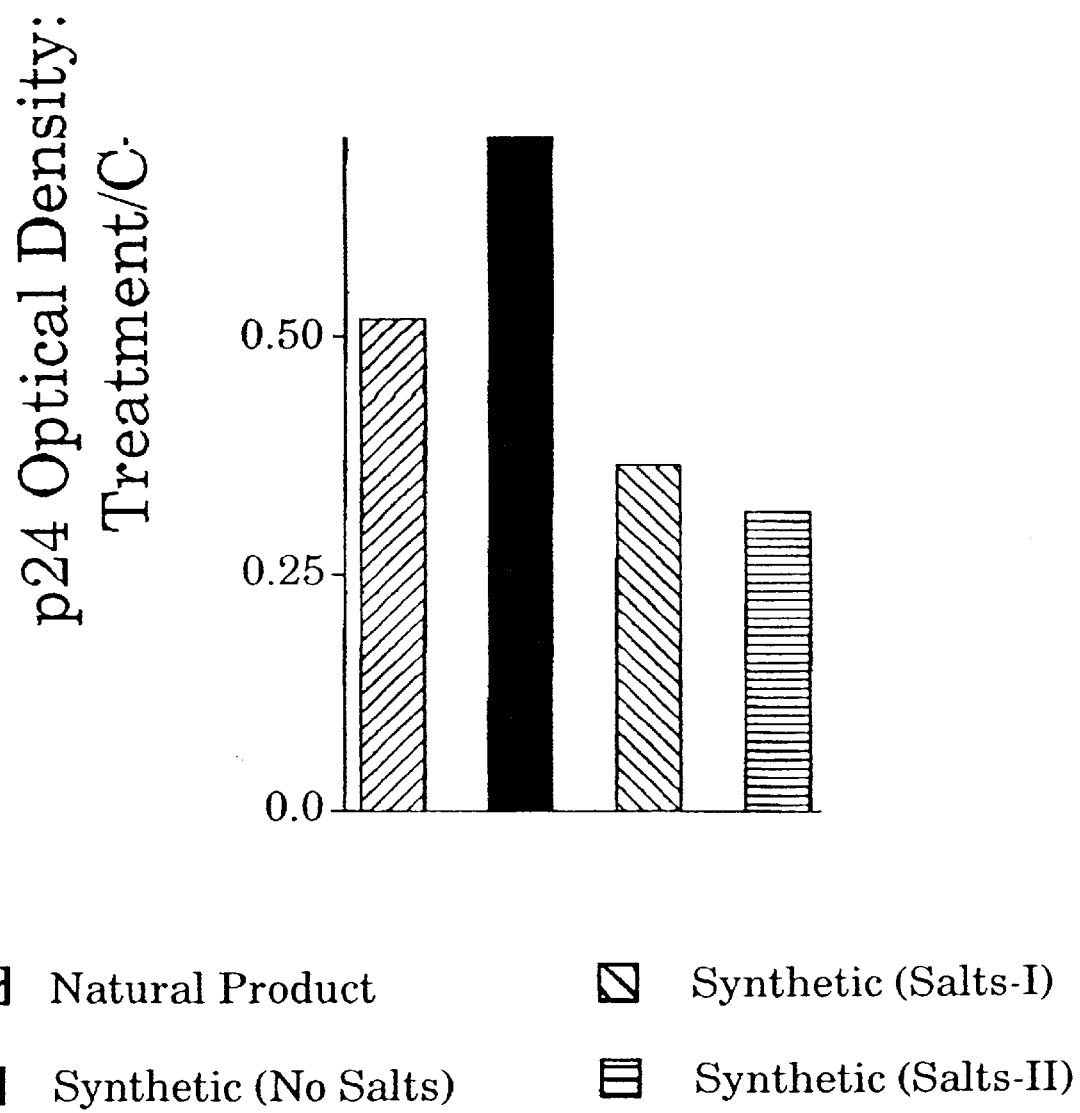
FIG. 4 shows a bar graph of the effects of adding inorganic salts to synthetic humic acid on treatment efficacy, as measured by p24 activity.

FIG. 4 shows the effects (relative to positive control) on the treatment efficacy of adding inorganic salts to synthetic humic acids, prepared as described in Examples 9, 10, and 11, on the p24 expression of HIV-positive cells as measured according to the procedures of Example 20. Separate suspensions of infected human peripheral blood mononuclear cells were treated with 25 µg/mL of each material. Treatments were maintained continuously for 6 days. HIV-1 was assessed via p24 production relative to positive control, i.e., p24 production in infected cells with no treatment. The result for natural-product humic acid shown for comparison.

The results showed almost no reduction in p24 expression for the synthetic humic acid without salts (prepared by the method of Example 9). By comparison, the synthetic humic acids containing salts (Examples 10 and 11) were effective at suppressing p24 expression, more so than was the natural-product material. Addition of salts to the solution therefore greatly increase the activity of the synthetic humic acid.

In the following Examples 22–47, several hundred milligrams of synthetic humic acid were prepared according to the procedures of Examples 12, 13, and 14. Natural-product humic acid was prepared by dialysis with subsequent freeze-drying as described in Examples 1–11. The human immunodeficiency anti-viral properties of these materials were assessed according to the methods described in Examples 22–47.

EXAMPLE 22

HIV Cytoprotection Properties of Natural-Product and Synthetic Humic Acids prepared according to Examples12–14

CEM-SS cells (obtained from the AIDS Research and Reference Reagent Repository, Bethesda, Md.) were passaged in T-75 flasks in tissue culture media [RPMI 1640 medium (no phenol red) with 10% fetal bovine serum (heat inactivated), 2 mM L-glutamine, 100 U/mL penicillin, 100 µg/mL streptomycin, and 10 µg/mL gentamycin]. On the day preceding the assay the cells were split 1:2 to ensure they were in an exponential growth phase at the time of infection. On the day of the assay the cells were collected by centrifugation, washed twice with tissue culture medium and resuspended at $5 \times 10^4$ cells per mL in fresh tissue culture medium. Total cell and viability counting was performed using a hemacytometer. Cell viability prior to the assay was determined by Trypan Blue dye exclusion and exceeded 95% in all cases. A pretitered aliquot of HIV-IRf (AIDS Research and Reference Reagent Repository, Bethesda, Md.), $5 \times 10^3$ cells, and compound (where appropriate) were placed into 0.2-cm round-bottom microtiter plates (final volume 200 µL). Each plate contained cell control wells (cells only), virus control wells (cells plus virus), drug toxicity control wells (cells plus drug only), drug colorimetric control wells (drug only), as well as experimental wells (drug plus cells plus virus). Cultures were incubated for 6 days at 37° C. and 5% $CO_2$, and antiviral activity and compound toxicity were determined by MTS staining. Activity was confirmed by both macroscopic and microscopic analysis of the assay.

Table 6 summarizes the results of the HIV cytoprotection studies. First, the inhibitory concentration values ($IC_{50}$) were determined in an initial series of experiments. The $IC_{50}$ value is the concentration at which 50% of the cells are prevented from being affected. The $IC_{50}$ value is therefore a measure of the effectiveness of the compound, where a low $IC_{50}$ value indicates that the compound is highly effective. The compound high-test concentration was then increased to 1 mg/mL in a second series of experiments in an attempt to determine toxic concentration ($TC_{50}$) values. The $TC_{50}$ value is the concentration of the compound at which 50% of the cells die. A low $TC_{50}$ value therefore indicates that the compound is very toxic to the cells. Also shown for comparison are the data observed for AZT (azidothymidine).

TABLE 6

| Compound | $IC_{50}$ | $TC_{50}$ | TI (=$IC_{50}/TC_{50}$) |
| --- | --- | --- | --- |
| AZT | 5.35 | >1 | — |
| Caffeic Acid Humate | 0.61 | 605 | 991 |
| Chlorogenic Acid Humate | 2.03 | 533 | 263 |
| Homogentisic Acid Humate | 3.46 | 158 | 46 |
| Natural-Product Humate | 0.78 | >1000 | >1282 |

[1]All concentrations in µg/mL.

The results showed that the humates were essentially non-cytotoxic at therapeutic dose concentrations. The natural-product humic acid and the synthetic humic acid produced from caffeic acid were also found to be more potent than the synthetic humic acids produced from chlorogenic and homogentisic acids by 3.3 and 4.4-fold, respectively. The natural-product humic acid and the synthetic humic acid produced from caffeic acid were roughly equipment, with $IC_{50}$ values of 0.61 and 0.78 µg/mL, respectively. The synthetic humic acid materials are therefore potent inhibitors of acute HIV infection in transformed CEM-SS T lymphoblastic cell lines.

AZT was more toxic than any of the humates by a factor of at least 150, as shown by the $TC_{50}$ value. AZT had a therapeutic index (TI) smaller by a factor of at least 50 than any of the humates, where the therapeutic index is the ratio of $IC_{50}/TC_{50}$, a measure of the effectiveness of the compound relative to the toxicity. A high therapeutic index shows that the compound is effective at a concentration that is far below the toxic level of the compound.

EXAMPLE 23

Antiviral Properties of Natural-Product and Synthetic Humic Acids prepared according to Examples 12–14 with Chronically-Infected Cells CEM-SS cells chronically infected with the SK-1 strain of HIV (obtained from the AIDS Research and Reference Reagent Repository, Bethesda, Md.) were treated as described in Example 22. Table 7 summarizes the results of the HIV cytoprotection studies obtained for the humic acid compounds with this cell line, where the $IC_{50}$ values were determined as described in Example 22. The data showed that the synthetic humic acid compounds were somewhat active in CEM-SS cells chronically infected with the SK-1 strain of HIV. Since chronically infected populations of cells are a mixture of uninfected dividing cells as well as long- and short-lived infected cells, a diminished antiviral activity in this model was expected if the humic acid compounds interacted with an antiviral target early in the HIV replication cycle. That is, the results indicated that the antiviral target for the humic acid compounds was occurring during early phases of HIV replication before integration and new virus transcription occurred.

TABLE 7

| Compound[1] | $IC_{50}$ | $TC_{50}$ | TI (=$IC_{50}/TC_{50}$) |
| --- | --- | --- | --- |
| Caffeic Acid Humate | 193.7 | 383 | 2.0 |
| Chlorogenic Acid Humate | 266.0 | 466 | 1.8 |
| Homogentisic Acid Humate | 152.8 | 212 | 1.4 |
| Natural-Product Humate | 130.8 | 566 | 4.3 |

[1]All concentrations in µg/mL.

EXAMPLE 24

HIV Replication Inhibition in Primary Lymphocytes and Monocytes by Natural-Product and Synthetic Humic Acids prepared according to Examples 12–14

PBMC isolation and blasting were carried out as follows: human peripheral blood monocular cells (PBMCs) were obtained from normal hepatitis and HIV-1 negative donors by ficoll hypaque gradient separation. Anti-coagulated blood was diluted 1:1 with Dulbecco's phosphate buffered saline without $Ca^{2+}$and $Mg^{2+}$(PBS) and layered over 14 mL of lymphocyte separation media in a 50 mL centrifuge tube. Tubes were then centrifuged for 30 minutes at 600 g. Banded PBLs were gently aspirated from the resulting interface and subsequently washed twice with PBS by low speed centrifugation. The mononuclear cells were counted, their viability determined by Trypan Blue dye exclusion, and they were then resuspended in RPMI 1640 medium supplemented with 15% FBS (heat inactivated), 2 mM L-glutamine, 100 U/mL penicillin, 100 µg/mL streptomycin, and 10 µg/mL gentamycin with 2 µg/mL phytohemagluttin (PHA) at $1 \times 10^6$ cells/mL. The cells were cultured for 48 to 72 h at 37° C., 5% $CO_2$. Following incubation, cells were collected by centrifugation, washed and resuspended in RPMI 1640 supplemented with 15% FBS (heat inactivated), 2 mM L-glutamine, 100 U/niL penicillin, 100 µg/mL streptomycin, and 10 µg/mL gentamycin with 20 U/mL recombinant IL-2 (R & D Systems, Minneapolis, Minn.). (IL-2 was included in the culture medium to maintain cell division initiated by PHA mitogenic stimulation.) The cultures were then maintained until use by a one-half culture volume change with fresh IL-2 containing medium every 3 days.

PBMC assays were carried out as follows: PBMCs from a minimum of 2 donors that had been blasted with PHA and IL-2 as described above were counted, their viability determined by Trypan Blue dye exclusion, and the cells were then mixed in equal ratios. Pooled donors were used to minimize the variability observed between individual donors (which could result from quantitative and qualitative differences in HIV infection and overall response to the PHA and IL-2 of primary lymphocyte populations). The cells were resuspended at $1 \times 10^6$ cells/mL in RPMI 1640 (without phenol red) supplemented with 15% fetal bovine serum (heat inactivated), 2 mM L-glutamine, 100 U/niL penicillin, 100 µg/mL streptomycin, 10 µg/mL gentamycin, and IL-2 (20 U/mnL, R&D Systems, Minneapolis, Minn.). Fifty microliters of cells were then distributed to the inner 60 wells of a 96-well round-bottom microtiter culture plate in a standard format developed by the Infectious Disease Research Department of Southern Research Institute (Frederick, Md.). Each plate contained cell control wells (cells only), virus control wells (cells plus virus), and experimental wells (drug plus cells plus virus). Serially-diluted compounds were added to the microtiter plate followed by the appropriate pre-titered strain of HIV-1. The RoJo strain of HIV was used. (RoJo is a low passage pediatric clinical isolate of HIV specifically isolated and developed in the laboratories of Southern Research Institute.) All samples were assayed in triplicate with a replicate plate without virus for the determination of compound toxicity. The final volume per well was 200 µL. The assay was incubated for 6 days in a humidified atmosphere at 37° C., 5% $CO_2$, after which supernatants were collected for analysis of RT activity and sister plates were analyzed for cell viability by MTS dye reduction.

To determine cell viability and quantify compound toxicity, MTS staining was carried out as follows: at assay termination the assay plates were stained with the soluble tetrazolium-based dye MTS (CellTiter Reagent Promega), 20 µL of MTS reagent being added to each well. (MTS is metabolized by the mitochondrial enzymes of metabolically active cells to a soluble formazan product, allowing the rapid quantitative analysis of cell viability and compound cytotoxicity. This reagent is a single stable solution that does not require preparation before use.) Incubation intervals were chosen based on empirically determined times for optimal dye reduction in each cell type. Adhesive plate sealers were used in place of lids, where the sealed plates were inverted several times to mix the soluble formazan product. Plates were read spectrophotometrically at 490 nm with a Molecular Devices Vmax plate reader.

Reverse transcriptase activity in cell-free supernatants was measured as follows: tritiated thymidine triphosphate (NEN) (TTP) was resuspended in distilled $H_2O$ at 5 Ci/mL. Poly rA and oligo dT were prepared as stock solutions and were kept at −20° C. The RT reaction buffer was prepared fresh on a daily basis and contained 125 µL 1.0 M EGTA, 125 µL $dH_2O$, 110 µL 10% SDS, 50 µL 1.0 M Tris (pH 7.4), 50 µL 1.0 M DTT, and 40 µL 1.0 M $MgCl_2$. These solutions were mixed together in a ratio of 2 parts TTP, 1 part poly rA:oligo dT, and 1 part reaction buffer. Ten microliters of this reaction mixture was placed in a round-bottom microtiter plate and 15 µL of virus-containing supernatant was added and mixed. The plate was incubated at 37° C. in a water bath with a solid support to prevent submersion of the plate, and incubated for 60 min. Following reaction, the reaction volume was spotted onto pieces of DE81 paper, washed 5 times for 5 minutes each in a 5% sodium phosphate buffer, 2 times for 1 minute each in distilled water, 2 times for 1 minute each in 70% ethanol, and then dried. Opti-Fluor 0 was added to each sample and incorporated radioactivity was then quantitated utilizing a Wallac 1450 Microbetaplus liquid scintillation counter.

Monocyte isolation, culture, infection, and assay were carried out as follows: peripheral blood monocytes were isolated from normal HIV-1 negative donors by plastic adherence following ficoll hypaque purification of the buffy coat, as described above for PBMCs. In many cases the same donor used to produce the PBMC populations was also 1 used to produce monocyte/macrophages; however, unlike PBMC populations, monocyte/macrophage donors were never pooled. Following a 2-hour adherence in RPMI 1640 (without phenol red) supplemented with 10% human pooled AB serum (heat inactivated), 2 mM L-glutamine, 100 U/mL penicillin, 100 µg/mL streptomycin, and 10 µg/mL gentamycin, cultures were washed to remove non-adherent cells. The monocytes were released from the plastic by vigorous pipetting with $Ca^{2+}$ and $Mg^{2+}$ free PBS. Adherent cells were assessed for purity by nonspecific esterase staining (a-napthyl butyrate specific esterase, Sigma Chemical Co.) and viability by Trypan Blue dye exclusion. They were counted and resuspended in RPMI 1640 supplemented with 10% fetal bovine serum (heat inactivated), 2 mM L-glutamine, 100 U/mL penicillin, 100 µg/mL streptomycin, and 10 µg/mL gentamycin at $1 \times 10^6$ monocytes per niL. The monocytes ($1 \times 10^5$ per 0.2-cm well) were then cultured for 6 days, allowing maturation of the cells to a macrophage-like phenotype. At day 6 the cultures were washed 3 times to remove any non-adherent cells and serially-diluted test compounds added. This was followed by the addition of a pre-titered amount of the Ba-L strain of HIV-1 obtained from the NIAID AIDS Research and Reference Reagent Repository. (Ba-L is a laboratory-adapted HWV isolate with tropism for monocyte/macrophages.) Cultures were washed a final time by media removal 24 h post infection, fresh compound was added, and the cultures continued for an additional six days. Monocyte/macrophage assays were performed using a standardized microtiter plate format developed by the Infectious Disease Research Department of Southern Research Institute, which used only the inner 60 wells of a 96-well plate for assay purposes. (The outer rows contained media and acted as an a evaporation barrier.) Each plate contained cell control wells (cells only), virus control wells (cells plus virus), and experimental wells (drug plus cells plus virus). HIV $p2^4$ antigen content, employed to assess virus replication, was measured at assay termination by a commercially-available p24 ELISA assay (Coulter). Toxicity of test materials was measured on replicate plates that did not receive virus, but were otherwise set up and treated identically to those receiving virus. AZT and/or ddC (HIV-1 reverse nucleoside transcriptase inhibitors) were used as positive control compounds and run in parallel with each determination.

Table 8 summarizes the antiviral effects of the humate compounds on HIV replication in primary lymphocytes. Table 9 summarizes the antiviral effects of the humate compounds on HIV replication in monocyte/macrophages. The humates were observed to be more potent by 2 to 5-fold in PBMCs than in monocyte/macrophages, with no cytotoxicity at 100 µg/mL for either. The synthetic humic acid produced from caffeic acid was the most active in PBMCs ($IC_{50}$ value of 0.28 µg/mL), while the synthetic humic acid produced from homogentisic acid was the most potent in monocyte/ macrophages ($IC_{50}$ value of 0.99 µg/mL). The synthetic humic acid materials are therefore potent inhibitors of acute HIV infection in primary peripheral blood cells.

TABLE 8

| Compound[1] | $IC_{50}$ | $TC_{50}$ | TI (=$IC_{50}/TC_{50}$) |
|---|---|---|---|
| AZT | 0.19 | >4 | >21 |
| Caffeic Acid Humate | 0.28 | >100 | >357 |
| Chlorogenic Acid Humate | 0.91 | >100 | >110 |
| Homogentisic Acid Humate | 0.43 | >100 | >233 |
| Natural-Product Humate | 0.92 | >100 | >109 |

[1]All concentrations in µg/mL.

TABLE 9

| Compound[1] | $IC_{50}$ | $TC_{50}$ | TI (=$IC_{50}/TC_{50}$) |
|---|---|---|---|
| AZT | 1.60 | >4 | >2.5 |
| Caffeic Acid Humate | 1.70 | >100 | >59 |
| Chlorogenic Acid Humate | 4.72 | >100 | >21 |
| Homogentisic Acid Humate | 0.99 | >100 | >101 |
| Natural-Product Humate | 2.64 | >100 | >38 |

[1]All concentrations in µg/mL.

EXAMPLE 25

HIV Viral Attachment Inhibition Properties of Natural-Product and Synthetic Humic Acids prepared according to Examples 12–14

The attachment inhibition assay was performed with HeLa CD4 LTR β-gal cells available from the AIDS Research and Reference Reagent Repository. Unmodified HeLa cells express the HIV coreceptor CXCR4, but not CD4. HeLa CD4 LTR β-gal cells are HeLa cells which express CD4 and contain a β-galactosidase enzyme under the transcriptional control of the HIV regulatory protein Tat. Thus, upon infection and virus integration, new Tat production results in transactivation of the LTR and production of β-galactosidase, which is then detected via chemiluminescence. The attachment fusion inhibitor Chicago Sky Blue was included as a positive control.

HeLa CD4 LTR β-gal cells were cultured in DMEM supplemented with 10% fetal bovine serum (heat inactivated), 2 mM L-glutamate, 100 U/ml penicillin, 100 μg/mL streptomycin, and the selection antibiotics hygromycin (100 μg/mL) and G418 (200 μtg/mL). Twenty-four hours prior to initiation of the assay the cells were trypsinized and counted, and $1 \times 10^4$ cells were placed in 0.2-cm wells in media without selection antibiotics. At 24 h the media was removed, compound in media was placed on the cells, and then incubated for 15 to 30 min at 37° C. A known titer of virus was then added to the wells and the incubation continued for 1 h. At the end of incubation the wells were washed 2 to 6 times with media and the culture continued for 48 h. At 48 h the media was removed and β-galactosidase enzyme expression was determined by chemiluminescence per the manufacturer's instructions (Tropix Gal-screen™, Bedford Mass.). This chemiluminescence method used a single solution containing cell lysis components and chemiluminescent substrates to detect activity in a single step. Compound toxicity was monitored on a sister plate using XTT dye reduction.

The interaction of gp120 and CD4 was also assessed with this assay. Immediately following the 1-h virus adsorption period the cells were washed 6 times and lysed. Cell-associated p24 antigen was then quantitated in the cell lysates by p24 antigen ELISA (Coulter). ELISA kits were purchased from Coulter Electronics. The assay was performed according to the manufacturer's instructions. Control curves were generated in each assay to quantitate accurately the amount of p24 antigen in each sample. Data were obtained by spectrophotometric analysis at 450 nm using a Molecular Devices Vmax plate reader. Final concentrations were calculated from the optical density values using the Molecular Devices Soft Max software package.

Table 10 shows the results of the general virus attachment work. All four humic acid congers were potent inhibitors of virus cell attachment, with the humic acid produced from chlorogenic acid being between 40 to 80-fold more potent than the other humic compounds.

TABLE 10

| Compound[1] | $IC_{50}$ | $TC_{50}$ | TI (=$IC_{50}/TC_{50}$) |
|---|---|---|---|
| Chicago Sky Blue | 0.53 | >10 | >18 |
| Caffeic Acid Humate | 0.44 | >1000 | >2272 |
| Chlorogenic Acid Humate | 0.01 | >1000 | >100 000 |

TABLE 10-continued

| Compound[1] | $IC_{50}$ | $TC_{50}$ | TI (=$IC_{50}/TC_{50}$) |
|---|---|---|---|
| Homogentisic Acid Humate | 0.88 | >1000 | >1136 |
| Natural-Product Humate | 0.48 | >1000 | >2083 |

[1]All concentrations in μg/mL.

Table 11 shows that the four humic compounds were 8-fold more efficacious at blocking the association of virus to the HeLa CD4 LTR β-gal cells via gp120/CD4 interaction than was the positive control. However, the humic acid produced from chlorogenic acid was no more potent at blocking this specific interaction than were the other humic compounds. The 60-fold differential in efficacy of the humic acid produced from chlorogenic acid for the general attachment assay versus that for the gp120/CD4 interaction indicates that, in fact, the humic compounds mediated antiviral activity through mechanisms additional to the prevention of the gp120/CD4 interaction.

TABLE 11

| Compound[1] | $IC_{50}$ | $TC_{50}$ | TI (=$IC_{50}/TC_{50}$) |
|---|---|---|---|
| Chicago Sky Blue | 2.06 | >10 | >5 |
| Caffeic Acid Humate | 0.74 | >1000 | >1353 |
| Chlorogenic Acid Humate | 0.69 | >1000 | >1449 |
| Homogentisic Acid Humate | 0.68 | >1000 | >1471 |
| Natural-Product Humate | 0.23 | >1000 | >4347 |

[1]All concentrations in μg/mL.

EXAMPLE 26

Time of Addition Assay

The studies performed in Examples 22–25 showed that the humates are inhibitors of HIV virus entry. This was demonstrated by their ability to prevent virus replication in an assay designed to monitor inhibition of virus replication via disruption of early phases of virus-cell interaction. The assessment of cell-associated p24 was also included in the initial assays. The cell-associated p24 assay provides a rough estimate of the ability of a compound to prevent the interaction of human immunodeficiency virus gp120 with cell-expressed CD4. The results showed that the humates mediate antiviral activity in part by preventing the initial interaction of human immunodeficiency virus with the cell. However, considering the general nature of the antiviral assays employed, the specific antiviral target for humates required further definition.

The time-of-addition assay uses the addition of known inhibitors of virus attachment, fusion and reverse transcription at various times post-infection to map the presence of these targets during a single round of infection assay. For example, it is well-known that the process of reverse transcription goes to completion in approximately 4 hours after the addition of human immunodeficiency virus to cells. The addition of a reverse transcriptase inhibitor prior to 4 hours will result in the inhibition of virus replication; while the addition after the completion of reverse transcription (i.e., after 4 hours) will not alter virus replication. Thus, the timed addition of known inhibitors of reverse transcription, virus attachment, and inhibitors of HIV coreceptor interactions, when employed in conjunction with techniques that follow the progress of reverse transcription, can be used to map inhibitor profiles.

The four humates are used in a time of addition assay in which virus replication is monitored by the induction of β-gal actosidase in HeLa CD4 LTR l-gal cells; and the completion of reverse transcription is monitored by PCR analysis of reverse transcription intermediates. The antiviral profiles (data not shown) of the humates are compared with that of known reverse transcriptase, attachment, and HIV coreceptor inhibitors.

EXAMPLE 27

Fusion Assay

The humates are tested for inhibition of the HIV fusion process with the HL2/3, HeLa CD4 LTR β-gal assay. HL2/3 cells express HIV Env on their cell surface and the Tat protein in their cytoplasma. Upon mixture with HeLa CD4 LTR-β-gal cells, the HL2/3 Env (gp120) interacts with CD4 on the HeLa CD4 LTR-β-gal cells. The cells fuse and the cytoplasmic contents mix. The Tat derived from the HL2/3 cells then transactivates the LTR r-gal reporter and stimulates β-gal actosidase enzyme production. Activity of the four humates in this assay (data not shown) correlates with inhibition of the gp120/CD4 interaction and virus cell fusion. The humates are found to be highly effective at inhibiting gp120/CD4 interaction and virus cell fusion.

EXAMPLE 28

Inhibition of GP120/CD4 Interaction

This assay uses recombinant gp120 and CD4 to assess the ability of the four humates to prevent the direct interaction of the gp120 and CD4 proteins. The four humates (data not shown) can interact directly with either gp120 or CD4 to prevent their association. The four humates are found to be highly effective at preventing association of gp120 and CD4.

EXAMPLE 29

Expansion of the GP120/CD4 Interaction

Epitope mapping of the interaction sites is carried out. These studies use antibodies with known interaction sites to map epitope expression on either CD4 or gp120, and can be used to identify specific compound/target protein interaction sites. The number of antibodies used is strictly dependent upon the number of anti-gp120 or CD4 antibodies available for these studies, but minimally uses 2 antibodies in the binding site and 2 outside the binding site. The total antibodies used for mapping does not exceed 10. The humates are found to associate with the binding site.

EXAMPLE 30

Activity in the HIV-Complex Attachment Assay

This assay uses the preformation of a human immunodeficiency virus/cell attachment fusion complex to assess the ability of the four humates to interact with the attachment fusion complex, to prevent human immunodeficiency virus entry after gp120/CD4 interaction, and to displace bound human immunodeficiency virus. The process of the interaction of cell CD4 and its chemokine coreceptor with human immunodeficiency virus gp120 and gp41 results in the formation of unique conformational targets with antiviral potential. In this assay, human immunodeficiency virus is allowed to attach to cells at 4° C. (gp120/CD4 interaction). Following this attachment phase excess virus is removed, the test compound is added and allowed to interact with the attachment/fusion complex. Following interaction, the ability of the compound to bind to the complex and prevent human immunodeficiency virus entry and/or the ability to displace virus from the cell surface is measured (data not shown). The humates are found to both prevent human immunodeficiency virus and displace virus from the cell surface.

EXAMPLE 31

Coreceptor Specificity of Inhibition

Human immunodeficiency virus employs the chemokine receptors CXCR4 and CCR5 as coreceptors to allow virus to enter target cells. Human immunodeficiency viruses may use one or both of the coreceptors to enter the cell, and in some cases may only use a particular coreceptor if both are present, although the second does not play a direct role in virus entry. Thus, the attachment/fusion complex may be radically different depending upon the coreceptor specified by the sequence of gp120 displayed on the virus. The antiviral activity of the four humates on both the CXCR5 and CCR5 coreceptors, either individually or when co-expressed, is measured (data not shown), that is, the potential of the compounds to interact differentially with the coreceptors is addressed. The humates are found to be nonspecific for the coreceptors.

EXAMPLE 32

Ability to Inhibit Syncytia Formation

Syncytia formation is the process whereby human immunodeficiency virus mediates the fusion of cells. The inhibition of syncytia formation usually occurs hand in hand with the prevention of virus entry; however, in some cases, the processes can be disassociated. Several compounds have been identified which will prevent virus infection at a post gp120/CD4 interaction, but fail to prevent syncytia formation. Since syncytia formation is employed as a measure of the results in many antiviral assays, the human immunodeficiency antiviral activity of the four humate compounds in terms of the inhibition of syncytia formation is measured (data not shown). The humates are found to be highly effective in inhibiting syncytia formation.

EXAMPLE 33

Virucidal Assays

Compounds can interact directly with human immunodeficiency virus and inactivate them via a variety of mechanisms, both active and passive, rendering them non-infectious. Virucidal activity can result from a compound binding to a virus and preventing cell-surface interactions, or it can enter the virus and alter structural elements that result in loss of infectivity. The four humates are tested for potential Virucidal activity (data not shown): compounds are exposed to cell-free human immunodeficiency virus and the virus is then assessed for infectivity after removal of the excess compound by centrifugation. The humates are found to be highly active in inhibiting the infectivity of the virus.

EXAMPLE 34

Secondary Virucidal Assay

The magnitude of human immunodeficiency virus inactivation exhibited by the four humate compounds in Example 33 is followed up in an additional study: human immunodeficiency virus with a known titer, i.e. 5 to 7 $Log_{10}$ $TCID_{50}$, is interacted with the compounds and the log reduction in virus infectivity is quantitated (data not shown). The humates are highly effective in reducing virus infectivity.

Although initial analysis of the antiviral activity of the four humate compounds suggests inhibition of virus entry as their mechanism of action, it is important to identify their activity in standard target-based antiviral assays. Inhibition in target-based assays using recombinant proteins can be either specific or non-specific in nature. Information gained from the Examples described above allows the assignment of a primary mechanism of action for the humates; however, the information gained from biochemical assays can be used in several additional ways, such as suggesting alternative mechanisms of action. Also, a second and possibly more important reason for performing these studies is to identify and eliminate potentially non-specific assays from consideration. Although this may seem a trivial point, knowing that a compound can non-specifically interact with reverse transcriptase, integrase or protease enzymes in a biochemical assay can help control reports of alternative activities that can confuse the literature and raise doubts about a compound's mode of action. Thus, although not necessarily providing specific anti-viral target information, the following Examples provide further important data on the synthetic humates prepared according to the procedures of Examples 12, 13, and 14; as well as the natural-product humic acid prepared by dialysis with subsequent freeze-drying as described in Examples 1–11.

EXAMPLE 35

Stability in Serum and AAGP

The stability of the humate compounds in increasing concentrations of human serum and α-1 acidic glycoprotein (AAGP) is an important pre-pharmacology parameter to assess during in vitro testing. Both nonnucleoside reverse transcriptase and protease inhibitors, in general as a class, lose significant antiviral activity when exposed to increasing serum concentration and AAGP due to interactions with serum proteins. Thus, assessment of the anti-viral activity of the four humate compounds under these conditions (data not shown) is used to identify potential caveats regarding their in vivo application to human immunodeficiency virus. The humates are found to be highly stable in the presence of high concentrations of human serum and a-1 acidic glycoprotein (AAGP).

EXAMPLE 36

Long-Term Exposure to Chronic Cells

Populations of chronically HIV-infected cells are a complex mixture of uninfected and infected cells. As described in Example 23, marginal human immunodeficiency antiviral efficacy for the four humate compounds with chronically infected cells was observed in a 6-day assay. Some activity, albeit marginal, is to be expected if the compounds' mechanism of action involves inhibition of virus entry: only new rounds of infection are prevented, while those cells that are chronically infected would continue to produce virus. The antiviral activity of the humate compounds in this assay could therefore have been masked by ongoing virus production. Ongoing human immunodeficiency virus production is compensated for in this Example by using a longer antiviral assay that results in serial passage of the cells, which in turn allows clearance of release virus products and amplification of effects that prevent new rounds of infection occurring.

Thus, chronically-infected CEM-SS cells are carried in the presence of the humate compounds for 28 days. At days 7, 14, 21, and 28 human immunodeficiency virus replication is assessed by measuring supernatant and intracellular p24 antigen expression and reverse transcriptase activity (data not shown). (Intracellular p24 expression is used to show that the compounds are not causing an effect on virus release.) The humates are found to be effective at inhibiting virus replication at periods of time of 14 days or more.

A primary concern of the FDA in advancing compounds to clinical trials is their ability to inhibit a wide range of virus types. Additionally, it is important to determine very early if a compound will inhibit SIV replication, so that the appropriate models for in vivo efficacy can be chosen. "Range of action" can also include activity against a variety of cell types. The following "range of action" Examples provide further important data on the synthetic humates prepared according to the procedures of Examples 12, 13, and 14; as well as the natural-product humic acid prepared by dialysis with subsequent freeze-drying as described in Examples 1–11.

EXAMPLE 37

Subtype Testing

HIV has 8 known subtypes. A subtype is a difference in the genotype of a particular HIV gene. The first subtypes identified, originally called clades, were based on genetic groupings in the Env gene. These subtype differences have now been extended to the Gag gene and other structural features of HIV as well as the Env gene. Subtype efficacy analysis is important in that subtypes may be associated with graphical regions and/or modes of transmission, e.g. B subtype is associated with developed countries (USA and Europe), while A is associated with underdeveloped countries. Thus, subtype testing is carried out in this Example to establish applicability of the human immunodeficiency antiviral response induced by the humate compounds to HIV replication and disease in general (data not shown). Testing is carried out against three strains of each subtype: A, B, C, D, E, F, G, and O, using low passage clinical isolates in PBMCs. The humates are found to be effective against all strains of each subtype.

EXAMPLE 38

Efficacy against other Retrobiruses

Testing of the four humate compounds is also carried out against SIV and HIV-2 (data not shown). Additionally, since the humates are inhibitors of HIV entry, they are also tested against an SIV carrying either an HIV Env gene or an Env SHIV gene (data not shown). This testing determines their efficacy against the Env SHIV as a prelude to in vivo non-human primate testing. Efficacy testing is carried out in human PBMCs. The humates are also effective against Env SHIV.

EXAMPLE 39

Testing against NSI and SI Viruses

HIV clinical isolates can be divided into non-syncytial inducing (NSI) and syncytial inducing (SI) virus types. The SI phenotype is usually related to late-stage viruses as infected individuals progress to AIDS, and the NSI viruses are associated with earlier phases of the disease. Syncytium induction is also directly linked to specific Env sequences.

The four humate compounds are tested in this Example against a panel of SI and NSI human immunodeficiency viruses (data not shown). Two of each virus type are used which, when employed in conjunction with the subtype panel, provides a strong range of action assessment for the compounds. (In addition to being designated SI and NSI, the viruses used for this panel are derived from low passage pediatric clinical isolates of HIV. Thus, efficacy against pediatric human immunodeficiency virus is also tested.) The humates are effective against pediatric human immunodeficiency virus.

EXAMPLE 40

LTNP Verses RSC

Two very important populations in the clinical spectrum of AIDS are the long term non-progressors (LTNP) and recent sero-converters (RSC). In this Example, the efficacy of the four humate compounds is tested against human immunodeficiency viruses derived from patients who have either had a very long latency period to appearance of disease or have just recently sero-converted following infection (data not shown). Two low-passage clinical isolates are employed for each category. The humates are effective against both viruses from patients who had a long latency period and who have just recently sero-converted following infection.

EXAMPLE 41

Range of Cell Action

In this Example a "panel" (i.e., a selection) of cell types is employed to measure HIV antiviral efficacy of the four humate compounds (data not shown). The panel represents specific cells that HIV may replicate in. The panel used in this Example includes H9 (additional T cell line; CEM-SS is a T cell line), U937 (monocytic cells), A55 (B Cells), CEMx174 (T×B fusion) and MT-2 cells (T cells infected with HTLV). The strength of this panel is two-fold. The first is that it strengthens the current range of action data (CEM-SS, PBMC and monocyte/macrophage) and, secondarily, since these cell lines are used by a number of different laboratories in their antiviral evaluations, it identifies any potential problems or advantages of assaying in these alternative systems. The humates are found to be effective against HIV in all of the cell types.

Development of resistance to a specific therapy or treatment is of primary concern in the evaluation of new antiviral drugs. For this reason the four humate compounds are tested in the following several Examples against human immunodeficiency viruses using assays that are purposely designed to promote drug resistance.

EXAMPLE 42

Testing against known Drug-Resistant Viruses variety of panels are currently available for testing compound efficacy against drug-resistant human immunodeficiency viruses. Since the data heretofore obtained as described in the preceding Examples demonstrate that the four humate compounds are potential inhibitors of HIV attachment, the following panel of human immunodeficiency viruses is employed for testing in this Example (data not shown):

1. Non-nucleoside reverse transcriptase inhibitor SJ3366-resistant human immunodeficiency virus with a dual mechanism of action involving HIV attachment.
2. Multi-drug-resistant human immunodeficiency virus derived from a highly experienced patient. Resistant to a number of protease and reverse transcriptase inhibitors currently used in HIV treatment.
3. AZT-resistant human immunodeficiency virus. Contains the four reverse transcriptase mutations (D67N, K70R, T215Y and K219Q) required to render a human immunodeficiency virus resistant to AZT. In this case the four humate compounds are demonstrated to be efficacious against a human immunodeficiency virus that is resistant to a well-known drug.
4. Conocurvone-resistant virus. Conocurvone is an attachment inhibitor; human immunodeficiency anti-viral drug resistance takes place by truncation of Env together with compensatory mutations.
5. Activity against a molecular cloned human immunodeficiency virus expressing the four mutations associated with AZT resistance and a key mutation either for resistance to nucleoside reverse transcriptase inhibitors (NTRI, L1001) or for non-nucleoside reverse transcriptase inhibitors (NNRTI, Y181 C).

The humates are found to be effective against all of the resistant viruses.

EXAMPLE 43

In Vitro Resistance Selection

A significant requirement of the FDA for advancement of new antivirals is determining their susceptibility to loss of activity due to generation of resistant viruses. In this Example in vivo resistance generation is promoted by serially passing virus in the presence of suboptimal escalating concentrations of the four humate compounds (data not shown). (Since the humates are attachment inhibitors, it is important to note that it is notoriously difficult to produce resistant virus with attachment inhibitor compounds. A year or more of passage is often required where, in some cases, resistance never develops. Thus, a 6-month resistance selection scheme was chosen for purposes of the current Example. The selection scheme includes efficacy testing carried out using CEM-SS cells, and a final verification of resistance in PBMCs if resistant virus were to be developed. If resistance were to be reached sooner than 6 months, the virus HIV Env gene will be sequenced in order to identify specific mutations.) The virus does not develop resistance even after six months.

Once specific mutations are identified a molecular clone of the mutation in the NL4-3 or IIIB strains is made to verify that the specific mutations are resistance-engendering. Since the four humate compounds are attachment inhibitors, work is carried out also on providing confirmation of resistance-engendering mutations based upon an HIV Env target (data not shown). (Since all known viruses engendered from attachment inhibitors have complex changes in the env gene, these studies are very complex. Additionally, there is evidence that there may be compensatory changes in gag genes to compensate for altered virus attachment.) The viruses are found not to develop resistance to the humates.

EXAMPLE 44

Combination Studies

Since current antiviral therapy is performed using combination chemotherapy, a primary concern is how a new human immunodeficiency antiviral drug will interact with a known antiviral drug. On the positive side this interaction can result in synergistic antiviral activity. On the negative side the two compounds may not be compatible and result in antagonistic antiviral activity or synergistic toxicities. And a third possibility is that the compounds are additive, and thus compatible without any interaction. Thus, in vitro combination testing in this Example addresses the potential synergy between human immunodeficiency anti-viral compounds. The Shipman and Prichard MacSynergy II Method is employed, which results in the generation of three-dimensional plots that identify compound interactions. The four humate compounds are tested for anti-viral efficacy in combination with AZT, two NNRTIs and two protease inhibitors, for a total of five combination assays (data not shown). (The protease inhibitors and NNRTIs are clinically approved inhibitors that are chosen based upon compound availability.) The humates are found to be synergistic with all of the compounds.

EXAMPLE 45

Topical Virucidal Testing

Since the four humate compounds have been shown in previous Examples to act as inhibitors of HIV virus entry and attachment, one very important area to be assessed is their efficacy as inhibitors of cell-to-cell transmission of HIV. At a recent conference (Microbiocides 2000: March, 2000; Arlington, Va.), it was noted that there is an urgent need for the development of new topical virucides to prevent vaginal and anal transmission of HIV. Virucides and inhibitors of HIV attachment and fusion were identified as the most likely arena for the development of these new therapeutics. Thus, assessment of the humates for inhibition of cell-to-cell transmission in topical virucide screening models is carried out in this Example. Since it is not known if vaginal transmission of HIV is CD4-dependent or-independent, screening models are employed that assess virus transmission under both conditions (data not shown). Additionally, since vaginal fluid is a high-protein environment, the testing is routinely performed with and without mucin in order to simulate a high protein environment. Finally, since the normal $H_2O_2$ producing microflora of the vagina (Lactobacillus) can control susceptibility to vaginal transmission of HIV, cytotoxicity testing for two strains of important Lactobacillus is also included in the work (data not shown). The humates are found to be effective inhibitors of cell to cell transmission in the topical microbiocide screening models.

In Vivo Efficacy in Animal Models

Efficacy testing in non-human primates with a representative synthetic humate compound, produced from chlorogenic acid as described in Example 16, is carried out as described in the following Examples using both a treatment model of chronically-infected macaques as well as a vaginal transmission model of SIV naive macaques.

EXAMPLE 46

Transmission Model

The in vivo model employed in this Example is the SHIV-macaque model using SHIV/SIV naive macaques. This model has been used to achieve mucosal infection reproducibly in naive animals. The core of the proposed study uses eight mature female macaques divided into two groups of four animals. The animals are purchased from a reputable supplier and quarantined at the Southern Research Institute facilities for the required period of time (6 weeks). During the quarantine period the animals are treated with progesterone to control their estrous cycle, which helps to optimize mucosal infection with the SHIV virus. They are also bled at least twice for control parameters. Animals are treated vaginally with the test compound mixed in carrier (n=4) or with carrier alone (n=4). Fifteen minutes after the treatment the animals are challenged vaginally with an infectious dose of the SHIV virus. All animals are followed for signs of infection using viral RNA load and DNA screening, flow cytometry, and the presence of viremia at least four times over the 8-week experiment. The animals are monitored for diagnostic blood parameters one week prior to treatment, during treatment, and eight weeks post treatment (data not shown). Blood cells, plasma, and serum are stored for confirmatory testing. None of the animals which were treated with the compound become infected.

EXAMPLE 47

Treatment Model

The second in vivo model uses chronically infected macaques. The same SHIV isolate is used as is employed in the mucosal transmission model. SHIV/SIV naive macaques (n=8) are purchased from a reputable supplier and quarantined at the Southern Research Institute facilities for the required period of time (6 weeks). Following release from quarantine, the animals are infected with the chosen SHIV virus by intravenous infusion. The animals are followed for the establishment of an infection and for stabilized viral RNA levels (approximately an additional six weeks). At this time the animals are ready for treatment with the test compound.

One group of four animals receives the test compound and another group of four animals serves as control. A treatment and follow up time of eight weeks is used. During this time animals are followed for signs of infection using viral RNA load and DNA screening, flow cytometry, and the presence of viremia at least four times over the 8-week experiment (data not shown). The animals are observed daily for signs of toxicity, including fluid intake, weight loss, food intake and general energy levels. The animals are monitored for diagnostic blood parameters one week prior to treatment, during treatment, and four weeks post treatment. Drug toxicity is monitored by routine serum chemistry and blood analysis. Blood cells, plasma, and serum are stored for confirmatory testing. No signs of toxicity are observed, and the animals which are treated with the test compound have marked reduction in the infection.

The Examples described above establish relevant human immunodeficiency antiviral data and efficacy of the synthetic humate compounds. The studies conform to current requirements put forth by the FDA for preclinical analysis of new anti-virals.

Pharmaceutical Compositions

Pharmaceutical compositions comprising compounds according to preferred embodiments can be administered by mouth in the form of tablets, capsules, solutions, emulsions, or suspensions; by inhalation, in the form of liquid, solid particles, or a spray; by absorption through the skin, by an appliance such as a transdermal patch; or by way of the rectum, in the form of suppositories. Administration can also take place parenterally, for example in the form of injectable solutions.

Tablets are prepared by mixing the Active Ingredient ("Active Ingredient" is one or more compounds inclusive of synthetic phenolic polymeric materials obtained by the methods of the preferred embodiments) with pharmaceutically inert, inorganic or organic carriers, diluents, and/or excipients. Examples of such excipients which can be used for tablets, include lactose, maize starch or derivatives thereof, talc, stearic acid or salts thereof. Examples of suitable excipients for soft gelatin capsules include vegetable oils, waxes, fats, semisolid and liquid polyols.

Suitable excipients for the preparation of solutions and syrups include water, polyols, sucrose, invert sugar and glucose.

Suitable excipients for injectable solutions include water, alcohols, polyols, glycerol, and vegetable oils.

These pharmaceutical compositions can additionally contain preservatives, solubilizers, stabilizers, wetting agents, emulsifiers, sweeteners, colorants, flavorings, buffers, coating agents and antioxidants.

Pharmaceutical compositions according to preferred embodiments to be administered by parenteral injection comprise pharmaceutically acceptable, preferably sterile aqueous or nonaqueous solutions, dispersions, suspensions or emulsions as well as sterile powders for reconstitution into sterile injectable solutions or dispersions just prior to use.

The active ingredient can also be made in microencapsulated form.

Method of Treatment

In accordance with one preferred embodiment, the compounds and pharmaceutical compositions may be used in the prophylaxis and/or treatment of disease or conditions in mammals, including humans. Such diseases or conditions include those effected by human immunodeficiency viruses. Methods of use include the step of administering a therapeutically effective amount of the active ingredient to a mammal in need thereof.

Preferably, the compounds of preferred embodiments are administered in the form of a pharmaceutical formulation. Thus, the compounds may be administered orally, parenterally, topically, rectally, vaginally and etc., in appropriate dosage units, as desired.

The term parenteral as used herein includes subcutaneous, intravenous, intraarterial, injection or infusion techniques, without limitation. The term, "topically" emcompasses administration rectally and by inhalation spray, as well as the more common routes of the skin and the mucous membranes of the mouth and nose.

Actual dosage levels of active ingredients in the pharmaceutical compositions may be varied so as to administer an amount of the active compound(s) that is effective to achieve the desired therapeutic response for a particular patient.

The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including the body weight, general health, diet, time and route of administration, combination with other drugs and the severity of the particular disease being treated.

Many modifications and variations of the embodiments described herein may be made without departing from the scope, as is apparent to those skilled in the art. The specific embodiments described herein are offered by way of example only.

What is claimed is:

1. A method for inhibiting and/or treating human immunodeficiency virus infections in a mammal comprising administering to the mammal an effective amount of a synthetic phenolic polymeric material, said synthetic phenolic material having been prepared by the following steps:
    a) dissolving in an aqueous solution at least one starting organic compound comprising at least one hydroxyl group and at least one carbonyl group or at least two hydroxyl groups on an aromatic structure;
    b) adjusting the pH of the aqueous solution resulting from step a) to between about 8 and 11;
    c) oxidizing the at least one starting organic compound solution resulting from step b);
    d) polymerizing the oxidized compound resulting from step c);
    e) adding at least one water soluble compound or salt selected from the group consisting of boric acid, borate salts, alkaline earth salts, transition metal salts, alkaline sulfides, alkaline earth sulfides, or transition metal sulfides to the aqueous solution resulting from step d); and
    f) removing molecules from the solution resulting from step e) below about 500 to about 10,000 daltons
    wherein pH of solutions from steps a) to f) is above 7.

2. The method according to claim 1, wherein the starting organic compound is selected from the group consisting of a compound represented by the Formula I:

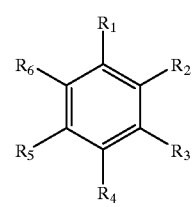

(I)

wherein $R_1, R_2, R_3, R_4, R_5$, and $R_6$ is a substituent selected from the group consisting of H, $CH_3$, $CH_2CH_3$, $(CH_2)_2CH_3$, $CH(CH_3)_2$, OH, $OCH_3$, CHO, $CO_2H$, $CO_2CH_3$, $CH_2OH$, $CH_2OCH_3$, $CH_2CHO$, $CH_2CO_2H$, $CH_2CO_2CH_3$, $(CH_2)_2OH$, $(CH_2)_2OCH_3$, $(CH_2)_2CHO$, $(CH_2)_2CO_2H$, $(CH_2)_2CO_2CH_3$, $CH(CH_3)OH$, $CH(CH_3)OCH_3$, $CH(CH_3)CHO$, $CH(CH_3)CO_2H$, $CH(CH_3)CO_2CH_3$, $CH(CH_3)CH_2OH$, $CH(CH_3)CH_2OCH_3$, $CH(CH_3)CH_2CHO$, $CH(CH_3)CH_2CO_2H$, $CH(CH_3)CH_2CO_2CH_3$, $CH(OH)_2$, $CH(OH)OCH_3$, $CH(OH)CHO$, $CH(OH)CO_2H$, $CH(OH)CO_2CH_3$, $CH(OCH_3)OH$, $CH(OCH_3)_2$, $CH(OCH_3)CHO$, $CH(OCH_3)CO_2H$, $CH(OCH_3)CO_2CH_3$, $CH(OH)CH_2OH$, $CH(OH)CH_2OCH_3$, $CH(OH)CH_2CHO$, $CH(OH)CH_2CO_2H$, $CH(OH)CH_2CO_2CH_3$, $CH(OCH_3)CH_2OH$, $CH(OCH_3)CH_2OCH_3$, $CH(OCH_3)CH_2CHO$, $CH(OCH_3)CH_2CO_2H$, $CH(OCH_3)CH_2CO_2CH_3$, $(CH_2)_3OH$, —$(CH_2)_3OCH_3$, $(CH_2)_3CHO$, $(CH_2)_3CO_2H$, $(CH_2)_3CO_2CH_3$, CHCHOH (cis or trans), $CHCHOCH_3$ (cis or trans), CHCHCHO (cis or trans), $CHCHCO_2H$ (cis or trans), $CHCHCO_2CH_3$ (cis or trans), $CH_2CHCHOH$ (cis or trans), $CH_2CHCHOCH_3$ (cis or trans), $CH_2CHCHCHO$ (cis or trans), $CH_2CHCHCO_2H$ (cis or trans), and $CH_2CHCHCO_2CH_3$ (cis or trans).

3. The method according to claim 2, wherein the compound comprises at least one hydroxyl group and at least one carboxylic acid group.

4. The method according to claim 1, wherein the starting organic compound is selected from the group consisting of

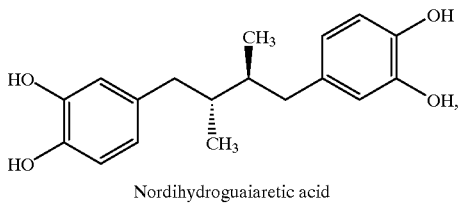
Nordihydroguaiaretic acid

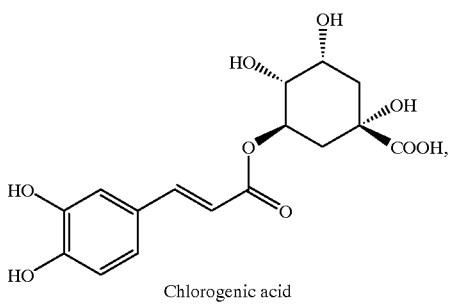
Chlorogenic acid

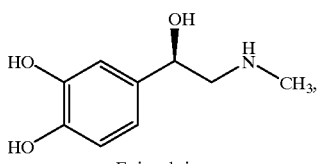
Epinephrine

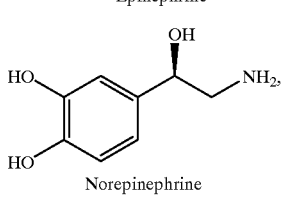
Norepinephrine

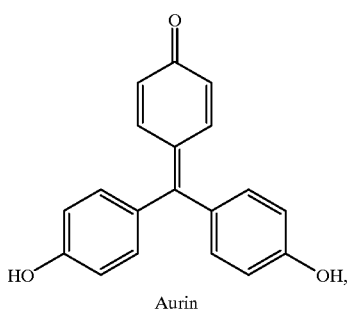
Aurin

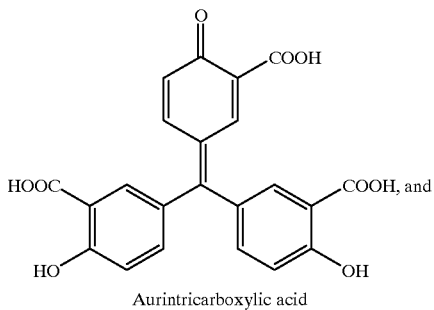
Aurintricarboxylic acid

-continued

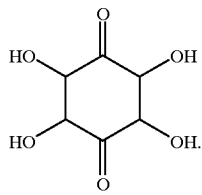
Tetrahydroxybenzoquinone

5. The method according to claim 1, wherein the aqueous solution in step a) comprises sodium hydroxide.

6. The method according to claim 1, wherein the method of preparation of the synthetic phenolic polymeric material further comprises a step, following step f), of:
   g) concentrating the solution resulting from step f).

7. The method according to claim 6, wherein the method of preparation of the synthetic phenolic polymeric material further comprises a step, following step g), of:
   h) removing water from the solution resulting from step g).

8. The method according to claim 1, wherein the human immunodeficiency virus infection is effected by a virus selected from the group consisting of HIV-1 and HIV-2.

9. The method according to claim 1, wherein administering the effective amount of synthetic phenolic polymeric material is performed systemically.

10. The method according to claim 1, wherein administering the effective amount of synthetic phenolic polymeric material is performed topically.

11. The method according to claim 1, further comprising administering an additional antiviral composition in combination with the effective amount of a synthetic phenolic polymeric material.

12. The method according to claim 11, wherein administering the effective amount of synthetic phenolic polymeric material and the antiviral composition is performed systemically.

13. The method according to claim 11, wherein administering the effective amount of synthetic phenolic polymeric material and the antiviral composition is performed topically.

14. The method of claim 1, wherein the synthetic phenolic material has been prepared by a method wherein step c) comprises adding an alkaline periodate salt or alkaline-earth periodate salt to the aqueous solution resulting from step b).

15. The method of claim 1, wherein the synthetic phenolic material has been prepared by a method wherein step d) comprises maintaining the temperature of the solution from step c) between about 20° C. and 100° C. for a period of at least about 30 minutes.

16. The method of claim 1, the synthetic phenolic material has been prepared by a method further comprising allowing the aqueous solution from step e) to stand with or without stirring at about 20° C. to 100° C. for at least about 2 hours after step e).

17. A method of inhibiting human immunodeficiency viral attachment to host cells in a mammal comprising administering to the mammal an effective amount of a synthetic phenolic polymeric material, said synthetic phenolic material having been prepared by the following steps:
   a) dissolving in an aqueous solution at least one starting organic compound comprising at least one hydroxyl group and at least one carbonyl group or at least two hydroxyl groups on an aromatic structure;
   b) adjusting the pH of the aqueous solution resulting from step a) to between about 8 and 11;

c) oxidizing the at least one starting organic compound solution resulting from step b);

d) polymerizing the oxidized compound resulting from step c);

e) adding at least one water soluble compound or salt selected from the group consisting of boric acid, borate salts, alkaline earth salts, transition metal salts, alkaline sulfides, alkaline earth sulfides, or transition metal sulfides to the aqueous solution resulting from step d); and f) removing molecules from the solution resulting from step e) below about 500 to about 10,000 daltons wherein pH of solutions from steps a) to f) is above 7.

18. The method according to claim 17, wherein the starting organic compound is selected from the group consisting of a compound represented by the formula I:

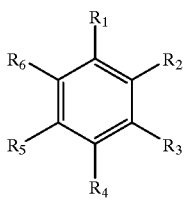

(I)

wherein $R_1, R_2, R_3, R_4, R_5,$ and $R_6$ is a substituent selected from the group consisting of H, $CH_3$, $CH_2CH_3$, $(CH_2)_2CH_3$, $CH(CH_3)_2$, OH, $OCH_3$, CHO, $CO_2H$, $CO_2CH_3$, $CH_2OH$, $CH_2OCH_3$, $CH_2CHO$, $CH_2CO_2H$, $CH_2CO_2CH_3$, $(CH_2)_2OH$, $(CH_2)_2OCH_3$, $(CH_2)_2CHO$, $(CH_2)_2CO_2H$, $(CH_2)_2CO_2CH_3$, $CH(CH_3)OH$, $CH(CH_3)OCH_3$, $CH(CH_3)CHO$, $CH(CH_3)CO_2H$, $CH(CH_3)CO_2CH_3$, $CH(CH_3)CH_2OH$, $CH(CH_3)CH_2OCH_3$, $CH(CH_3)CH_2CHO$, $CH(CH_3)CH_2CO_2H$, $CH(CH_3)CH_2CO_2CH_3$, $CH(OH)_2$, $CH(OH)OCH_3$, $CH(OH)CHO$, $CH(OH)CO_2H$, $CH(OH)CO_2CH_3$, $CH(OCH_3)OH$, $CH(OCH_3)_2$, $CH(OCH_3)CHO$, $CH(OCH_3)CO_2H$, $CH(OCH_3)CO_2CH_3$, $CH(OH)CH_2OH$, $CH(OH)CH_2OCH_3$, $CH(OH)CH_2CHO$, $CH(OH)CH_2CO_2H$, $CH(OH)CH_2CO_2CH_3$, $CH(OCH_3)CH_2OH$, $CH(OCH_3)CH_2OCH_3$, $CH(OCH_3)CH_2CHO$, $CH(OCH_3)CH_2CO_2H$, $CH(OCH_3)CH_2CO_2CH_3$, $(CH_2)_3OH$, $-(CH_2)_3OCH_3$, $(CH_2)_3CHO$, $(CH_2)_3CO_2H$, $(CH_2)_3CO_2CH_3$, CHCHOH (cis or trans), $CHCHOCH_3$ (cis or trans), CHCHCHO (cis or trans), $CHCHCO_2H$ (cis or trans), $CHCHCO_2CH_3$ (cis or trans), $CH_2CHCHOH$ (cis or trans), $CH_2CHCHOCH_3$ (cis or trans), $CH_2CHCHCHO$ (cis or trans), $CH_2CHCHCO_2H$ (cis or trans), and $CH_2CHCHCO_2CH_3$ (cis or trans).

19. The method according to claim 18, wherein the compound comprises at least one hydroxyl group and at least one carboxylic acid group.

20. The method according to claim 17, wherein the starting organic compound is selected from the group consisting of

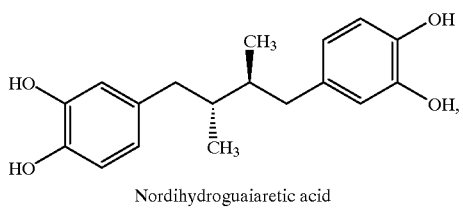

Nordihydroguaiaretic acid

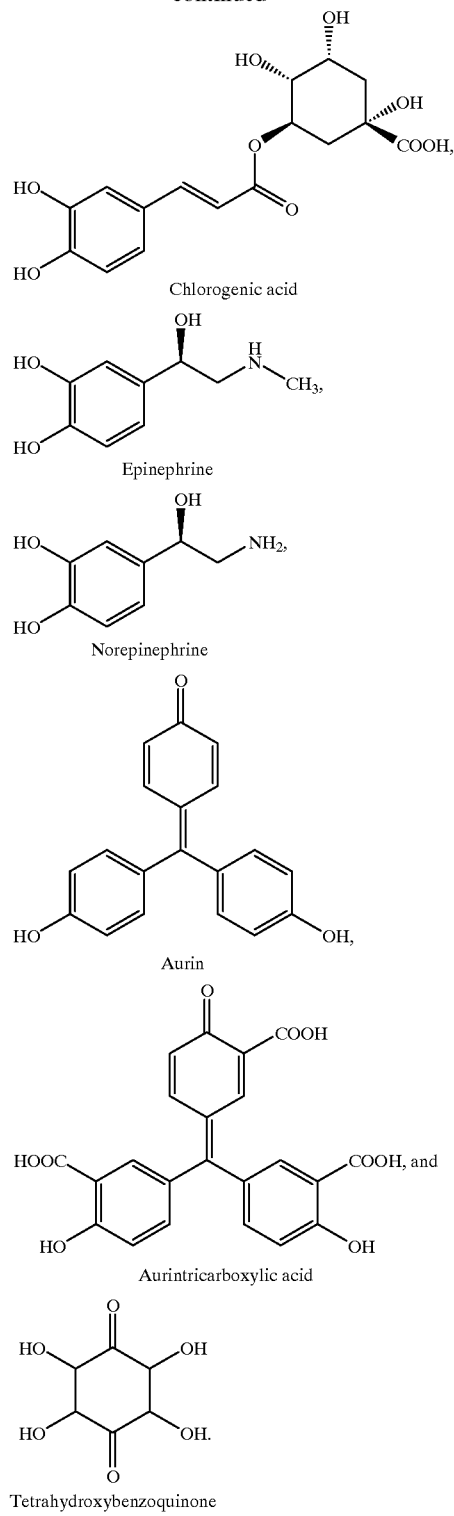

Chlorogenic acid

Epinephrine

Norepinephrine

Aurin

Aurintricarboxylic acid, and

Tetrahydroxybenzoquinone

21. The method according to claim 17, wherein the aqueous solution in step a) comprises sodium hydroxide.

22. The method according to claim 17, wherein the method of preparation of the synthetic phenolic polymeric material further comprises a step, following step f), of:

g) concentrating the solution resulting from step f).

23. The method according to claim 17, wherein the method of preparation of the synthetic phenolic polymeric material further comprises a step, following step g), of:

h) removing water from the solution resulting from step g).

24. The method according to claim 17, wherein the human immunodeficiency virus infection is effected by a virus selected from the group consisting of HIV-1 and HIV-2.

25. The method according to claim 17, wherein administering the effective amount of synthetic phenolic polymeric material is performed systemically.

26. The method according to claim 17, wherein administering the effective amount of synthetic phenolic polymeric material is performed topically.

27. The method according to claim 17, farther comprising administering an additional antiviral composition in combination with the effective amount of a synthetic phenolic polymeric material.

28. The method according to claim 27, wherein administering the effective amount of synthetic phenolic polymeric material and the antiviral composition is performed systemically.

29. The method according to claim 27, wherein administering the effective amount of synthetic phenolic polymeric material and the antiviral composition is performed topically.

30. The method of claim 17, wherein the synthetic phenolic material has been prepared by a method wherein step c) comprises adding an alkaline periodate salt or alkaline-earth periodate salt to the aqueous solution resulting from step b).

31. The method of claim 17, wherein the synthetic phenolic material has been prepared by a method wherein step d) comprises maintaining the temperature of the solution between about 20° C. and 100° C. for a period of at least about 30 minutes.

32. The method of claim 17, the synthetic phenolic material has been prepared by a method further comprising allowing the aqueous solution from step e) to stand with or without stirring at about 20° C. to 100° C. for at least about 2 hours after step e).

* * * * *